US012569152B2

(12) United States Patent
Burton et al.

(10) Patent No.: US 12,569,152 B2
(45) Date of Patent: Mar. 10, 2026

(54) METHOD TO NON-INVASIVELY ASSESS ELEVATED LEFT VENTRICULAR END-DIASTOLIC PRESSURE

(71) Applicant: Analytics for Life Inc., Toronto (CA)

(72) Inventors: Timothy William Fawcett Burton, Toronto (CA); Shyamlal Ramchandani, Kingston (CA); Ali Khosousi, North York (CA); Farhad Fathieh, North York (CA); Mohammad Firouzi, Toronto (CA); Emmanuel Lange, Toronto (CA); Abhinav Doomra, North York (CA)

(73) Assignee: Analytics for Life Inc., Toronto (CA)

( * ) Notice: Subject to any disclaimer, the term of this patent is extended or adjusted under 35 U.S.C. 154(b) by 506 days.

(21) Appl. No.: 17/891,522

(22) Filed: Aug. 19, 2022

(65) Prior Publication Data

US 2023/0071467 A1     Mar. 9, 2023

Related U.S. Application Data

(60) Provisional application No. 63/235,974, filed on Aug. 23, 2021, provisional application No. 63/236,072, (Continued)

(51) Int. Cl.
A61B 5/024     (2006.01)
A61B 5/00     (2006.01)
A61B 5/021     (2006.01)

(52) U.S. Cl.
CPC ...... *A61B 5/02427* (2013.01); *A61B 5/02108* (2013.01); *A61B 5/7203* (2013.01); *A61B 5/7264* (2013.01)

(58) Field of Classification Search
CPC ............ A61B 5/02427; A61B 5/02108; A61B 5/7203; A61B 5/7264
See application file for complete search history.

(56) References Cited

U.S. PATENT DOCUMENTS 7,314,451 B2    1/2008   Halperin et al.
8,923,958 B2    12/2014   Gupta et al.
(Continued)

FOREIGN PATENT DOCUMENTS

EP       3841967 A1    6/2021
WO    2010084211 A1    7/2010
(Continued)

OTHER PUBLICATIONS

Galiatsatos et al.; Usefulness of a Noninvasive Device to Identify Elevated Left Ventricular Filling Pressure Using Finger Photoplethysmography During a Valsalva Maneuver. The American Journal of Cardiology; vol. 119, Issue 7, Apr. 1, 2017, pp. 1053-1060 (Year: 2017).*
(Continued)

*Primary Examiner* — Chao Sheng
(74) *Attorney, Agent, or Firm* — Meunier Carlin & Curfman LLC

(57) ABSTRACT

A clinical evaluation system and method are disclosed that facilitate the use of features or parameters extracted from biophysical signals in a model or classifier (e.g., a machine-learned classifier) to estimate metrics associated with the physiological state of a patient, including for the presence or non-presence of elevated left ventricular end-diastolic pressure (elevated LVEDP), as an example indicator of a disease medical condition that could be assessed by using the system and method described herein.

15 Claims, 12 Drawing Sheets

Related U.S. Application Data filed on Aug. 23, 2021, provisional application No. 63/235,960, filed on Aug. 23, 2021, provisional application No. 63/235,968, filed on Aug. 23, 2021, provisional application No. 63/235,966, filed on Aug. 23, 2021, provisional application No. 63/236,193, filed on Aug. 23, 2021, provisional application No. 63/235,963, filed on Aug. 23, 2021, provisional application No. 63/235,971, filed on Aug. 23, 2021.

(56) References Cited

U.S. PATENT DOCUMENTS

| | | | |
|---|---|---|---|
| 9,289,150 | B1 | 3/2016 | Gupta et al. |
| 9,408,543 | B1 | 8/2016 | Gupta et al. |
| 9,597,021 | B1 | 3/2017 | Gupta et al. |
| 9,655,536 | B2 | 5/2017 | Gupta et al. |
| 9,737,229 | B1 | 8/2017 | Gupta et al. |
| 9,910,964 | B2 | 3/2018 | Burton et al. |
| 9,955,883 | B2 | 5/2018 | Gupta et al. |
| 9,968,265 | B2 | 5/2018 | Burton et al. |
| 9,968,275 | B2 | 5/2018 | Gupta et al. |
| 10,039,468 | B2 | 8/2018 | Gupta et al. |
| 10,140,421 | B1 | 11/2018 | Bernard et al. |
| 10,292,596 | B2 | 5/2019 | Shadforth et al. |
| 10,362,950 | B2 | 7/2019 | Gupta et al. |
| 10,542,897 | B2 | 1/2020 | Gupta et al. |
| 10,566,091 | B2 | 2/2020 | Burton et al. |
| 10,566,092 | B2 | 2/2020 | Burton et al. |
| 10,672,518 | B2 | 6/2020 | Burton et al. |
| 10,806,349 | B2 | 10/2020 | Shadforth et al. |
| 2007/0118028 | A1 | 5/2007 | Kitajima et al. |
| 2014/0257122 | A1 | 9/2014 | Ong et al. |
| 2016/0022164 | A1 | 1/2016 | Brockway et al. |
| 2016/0378936 | A1 | 12/2016 | Burton et al. |
| 2017/0251985 | A1 | 9/2017 | Howard |
| 2017/0277858 | A1 | 9/2017 | Okubo et al. |
| 2018/0000374 | A1 | 1/2018 | Gupta et al. |
| 2018/0064400 | A1 | 3/2018 | Chbat et al. |
| 2018/0177415 | A1 | 6/2018 | Madl |
| 2018/0249960 | A1 | 9/2018 | Gupta et al. |
| 2018/0261326 | A1 | 9/2018 | Burton et al. |
| 2019/0026430 | A1 | 1/2019 | Grouchy et al. |
| 2019/0026431 | A1 | 1/2019 | Grouchy et al. |
| 2019/0065970 | A1 | 2/2019 | Bonutti et al. |
| 2019/0104951 | A1 | 4/2019 | Valys et al. |
| 2019/0150867 | A1* | 5/2019 | Itou ......................... A61B 6/504 |
| 2019/0200893 | A1 | 7/2019 | Grouchy et al. |
| 2019/0214137 | A1 | 7/2019 | Gupta et al. |
| 2019/0313926 | A1 | 10/2019 | Gupta et al. |
| 2019/0365265 | A1 | 12/2019 | Grouchy et al. |
| 2019/0384757 | A1 | 12/2019 | Garrett et al. |
| 2019/0385711 | A1 | 12/2019 | Shriberg et al. |
| 2020/0029842 | A1 | 1/2020 | Felix et al. |
| 2020/0085311 | A1* | 3/2020 | Tzvieli ................... A61B 5/748 |
| 2020/0170527 | A1* | 6/2020 | Kale ................... A61B 5/7267 |
| 2020/0205739 | A1* | 7/2020 | Garrett ................... G16H 50/30 |
| 2020/0205745 | A1 | 7/2020 | Khosousi et al. |
| 2020/0211713 | A1* | 7/2020 | Shadforth .............. G16H 50/50 |
| 2020/0229724 | A1 | 7/2020 | Gupta et al. |
| 2020/0335217 | A1 | 10/2020 | Burton et al. |
| 2020/0367810 | A1 | 11/2020 | Shouldice et al. |
| 2020/0397322 | A1 | 12/2020 | Paak et al. |
| 2020/0397324 | A1 | 12/2020 | Paak et al. |
| 2021/0104321 | A1 | 4/2021 | Lipsky et al. |
| 2021/0212582 | A1 | 7/2021 | Fathieh et al. |
| 2022/0019256 | A1 | 1/2022 | Sung et al. |
| 2022/0192596 | A1 | 6/2022 | Fathieh et al. |
| 2022/0195296 | A1 | 6/2022 | Lastusaari et al. |
| 2023/0054371 | A1 | 2/2023 | Shadforth et al. |
| 2023/0055617 | A1 | 2/2023 | Lange et al. |
| 2023/0071085 | A1 | 3/2023 | Doomra |
| 2023/0072281 | A1 | 3/2023 | Fathieh et al. |
| 2023/0075570 | A1 | 3/2023 | Fathieh |
| 2023/0075634 | A1 | 3/2023 | Fathieh et al. |
| 2023/0076069 | A1 | 3/2023 | Lange et al. |
| 2023/0127355 | A1 | 4/2023 | Paak et al. |

FOREIGN PATENT DOCUMENTS

| | | |
|---|---|---|
| WO | 2017033164 A1 | 3/2017 |
| WO | 2017055880 A | 4/2017 |
| WO | 2017221221 A1 | 12/2017 |
| WO | 2018158749 A1 | 9/2018 |
| WO | 2019077414 A1 | 4/2019 |
| WO | 2019130272 A1 | 7/2019 |
| WO | 2019130273 A1 | 7/2019 |
| WO | 2019234587 A1 | 12/2019 |
| WO | 2019244043 A1 | 12/2019 |
| WO | 2020136569 A1 | 7/2020 |
| WO | 2020136570 A1 | 7/2020 |
| WO | 2020136571 A1 | 7/2020 |
| WO | 2021130709 A1 | 7/2021 |
| WO | 2023026158 A1 | 3/2023 |

OTHER PUBLICATIONS

Breiman, "Bagging predictors," Machine Learning, 24(2), 123-140, 1996.

Breiman, "Random Forests," Machine Learning, 45(1), 5-32, 2001.

Chen, Tianqi; Guestrin, Carlos (2016). "XGBoost: A Scalable Tree Boosting System," Proceedings of the 22nd ACM SIGKDD International Conference on Knowledge Discovery and Data Mining, San Francisco, CA, USA, Aug. 13-17, 2016. ACM. pp. 785-794.

Fathieh, Farhad, et al. "Predicting cardiac disease from interactions of simultaneously-acquired hemodynamic and cardiac signals." Computer Methods and Programs in Biomedicine 202 (2021): 105970.

Liu, F.T., Ting, K.M. and Zhou, Z.H., Dec. 2008. Isolation forest. In 2008 eighth IEEE international conference on data mining (pp. 413-422). IEEE.

Mancuso G, Strachan S, Capey S, 2019, 'Sequential testing in high stakes OSCE: a stratified cross-validation approach', MedEdPublish, 8, [2], 62, https://doi.org/10.15694/mep.2019. 000132.1.

Mielniczuk, Lisa M., et al. "Left ventricular end-diastolic pressure and risk of subsequent heart failure in patients following an acute myocardial infarction." Congestive Heart Failure 13.4 (2007): 209-214.

Zhang et al., "Facial Emotion Recognition Based on Biorthogonal Wavelet Entropy, Fuzzy Support Vector Machine, and Stratified Cross Validation," in IEEE Access, vol. 4, pp. 8375-8385, 2016, doi: 10.1109/ACCESS.2016.2628407.

Zou and T. Hastie, "Regularization and variable selection via the elastic net," Journal of the Roy. Statist. Soc., ser. B, vol. 67, No. 2, pp. 301-320, 2005.

International Search Report and Written Opinion issued for Application No. PCT/IB2022/057812, dated Nov. 2022.

\* cited by examiner

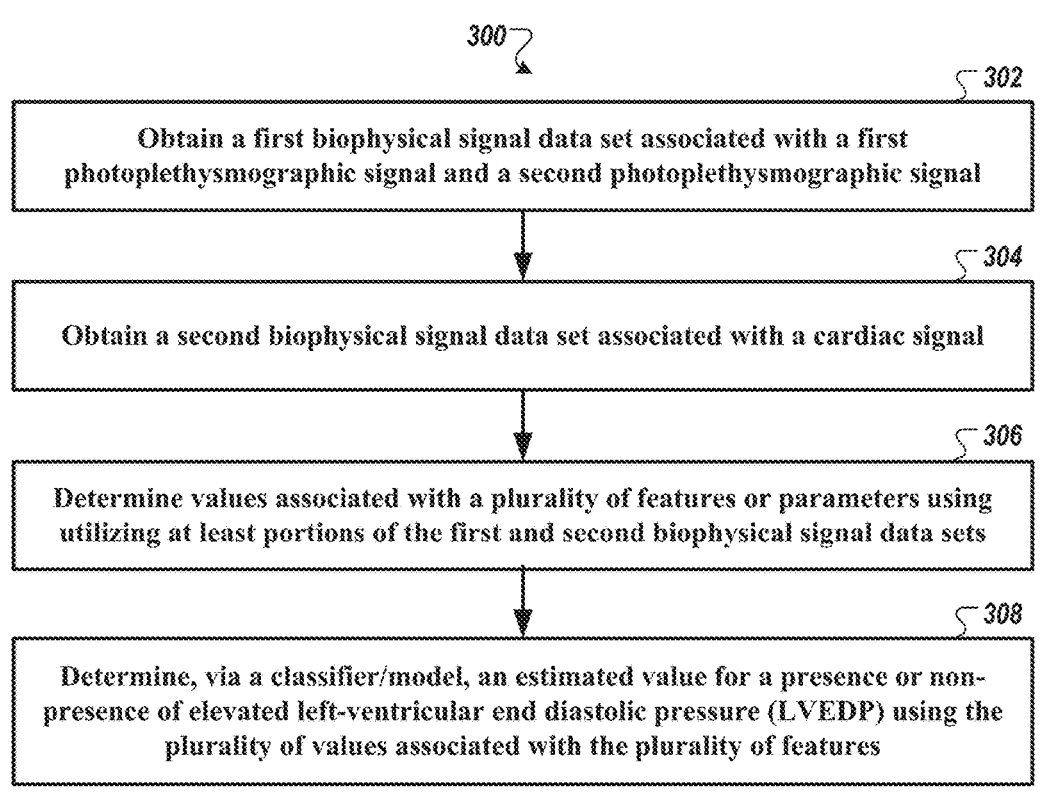

*300*

*302*

Obtain a first biophysical signal data set associated with a first photoplethysmographic signal and a second photoplethysmographic signal

*304*

Obtain a second biophysical signal data set associated with a cardiac signal

*306*

Determine values associated with a plurality of features or parameters using utilizing at least portions of the first and second biophysical signal data sets

*308*

Determine, via a classifier/model, an estimated value for a presence or non-presence of elevated left-ventricular end diastolic pressure (LVEDP) using the plurality of values associated with the plurality of features

FIG. 3A

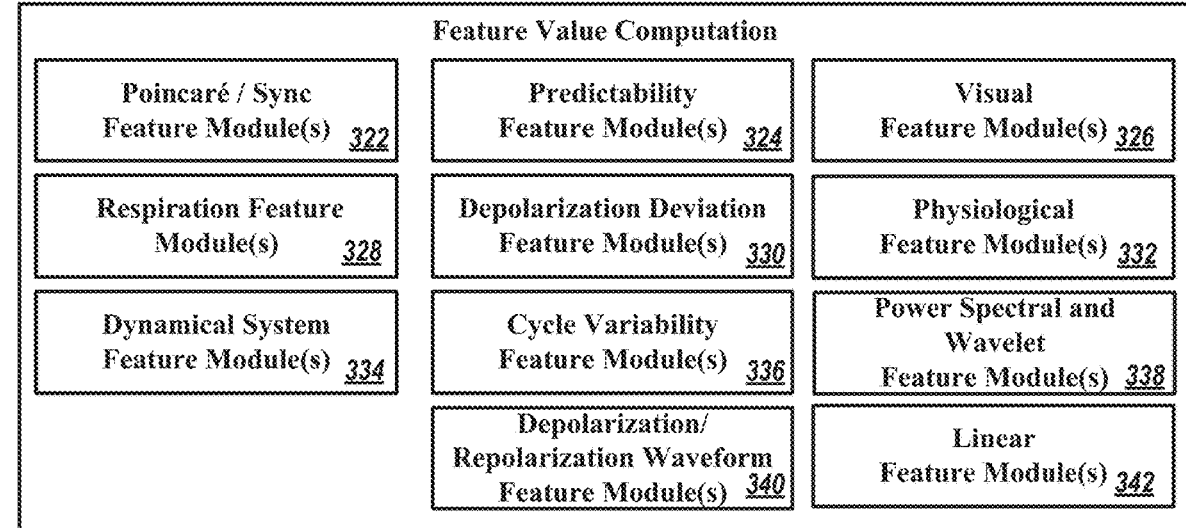

*122a*

Feature Value Computation

| Poincaré / Sync Feature Module(s) 322 | Predictability Feature Module(s) 324 | Visual Feature Module(s) 326 |
|---|---|---|
| Respiration Feature Module(s) 328 | Depolarization Deviation Feature Module(s) 330 | Physiological Feature Module(s) 332 |
| Dynamical System Feature Module(s) 334 | Cycle Variability Feature Module(s) 336 | Power Spectral and Wavelet Feature Module(s) 338 |
| | Depolarization/ Repolarization Waveform Feature Module(s) 340 | Linear Feature Module(s) 342 |

FIG. 3B

| | Hyp Param A = 1 _724_ | Hyp Param A = 2 _720_ | Hyp Param A = 3 _724_ |
|---|---|---|---|
| Hyp Param B = 0.1 _724_ | 0.60 | 0.68 ⟋712 | 0.68 |
| Hyp Param B = 0.5 _722_ | 0.64 ⟋714 | 0.67 ⟋710 | 0.65 ⟋718 |
| Hyp Param B = 0.9 _724_ | 0.64 | 0.66 ⟋716 | 0.66 |

*(CONT. 2)*

*(CONT. 3)*

*(CONT. 4)*

METHOD TO NON-INVASIVELY ASSESS ELEVATED LEFT VENTRICULAR END-DIASTOLIC PRESSURE

RELATED APPLICATION

This US application claims priority to, and the benefit of, U.S. Provisional Patent Application No. 63/235,960, filed Aug. 23, 2021, entitled "Method and System to Non-Invasively Assess Elevated Left Ventricular End-Diastolic Pressure"; U.S. Provisional Patent Application No. 63/236, 072, filed Aug. 23, 2021, entitled "Methods and Systems for Engineering Visual Features From Biophysical Signals for Use in Characterizing Physiological Systems"; U.S. Provisional Patent Application No. 63/235,963, filed Aug. 23, 2021, entitled "Methods and Systems for Engineering Power Spectral Features From Biophysical Signals for Use in Characterizing Physiological Systems"; U.S. Provisional Patent Application No. 63/235,966, filed Aug. 23, 2021, entitled "Method and System for Engineering Rate-Related Features From Biophysical Signals for Use in Characterizing Physiological Systems"; U.S. Provisional Patent Application No. 63/235,968, filed Aug. 23, 2021, entitled "Methods and Systems for Engineering Wavelet-Based Features From Biophysical Signals for Use in Characterizing Physiological Systems"; U.S. Provisional Patent Application No. 63/235,971, filed Aug. 23, 2021, entitled "Methods and Systems for Engineering photoplethysmographic Waveform Features for Use in Characterizing Physiological Systems"; U.S. Provisional Patent Application No. 63/236,193, filed Aug. 23, 2021, entitled "Methods and Systems for Engineering Cardiac Waveform Features From Biophysical Signals for Use in Characterizing Physiological Systems"; U.S. Provisional Patent Application No. 63/235,974, filed Aug. 23, 2021, entitled "Methods and Systems for Engineering Conduction Deviation Features From Biophysical Signals for Use in Characterizing Physiological Systems," each of which is incorporated by reference herein in its entirety.

FIELD OF THE INVENTIONS

The present disclosure generally relates to methods and systems, and its development system and environment, that can be used to assess for the presence, non-presence, severity, and/or localization of pathologies or indication of one, utilizing biophysical measurements, including in the estimation of the presence of elevated left-ventricular end-diastolic pressure (LVEDP) using cardiac and photoplethysmographic-related measurements.

BACKGROUND

There are numerous methods and systems for assisting a healthcare professional in diagnosing disease. Some of these involve the use of invasive or minimally invasive techniques, radiation, exercise or stress, or the use of pharmacological agents, sometimes in combination, with their attendant risks and other disadvantages.

Diastolic heart failure, a major cause of morbidity and mortality, is defined as symptoms of heart failure in a patient with preserved left ventricular function. It is characterized by a stiff left ventricle with decreased compliance and impaired relaxation leading to increased end-diastolic pressure in the left ventricle, which is measured through left heart catheterization. The current clinical standard of care for diagnosing pulmonary hypertension (PH), and for pulmonary arterial hypertension (PAH), in particular, involves a cardiac catheterization of the right side of the heart that directly measures the pressure in the pulmonary arteries. Coronary angiography is the current standard of care used for the assessment of coronary arterial disease (CAD) as determined through the coronary lesions described by a treating physician. Non-invasive imaging systems such as magnetic resonance imaging and computed tomography require specialized facilities to acquire images of blood flow and arterial blockages of a patient that are reviewed by radiologists.

It is desirable to have a system that can assist healthcare professionals in the diagnosis of cardiac disease and various other diseases and conditions without the aforementioned disadvantages.

SUMMARY

A clinical evaluation system and method are disclosed that facilitate the use of features or parameters extracted from biophysical signals in a model or classifier (e.g., a machine-learned classifier) to estimate metrics associated with the physiological state of a patient, including for the presence or non-presence of elevated left ventricular end-diastolic pressure (elevated LVEDP), as an example indicator of a disease medical condition that could be assessed by using the system and method described herein. The biophysical signals are acquired, in preferred embodiments, non-invasively from surface sensors such as placed on a patient while the patient is at rest. The estimated metric may be used to assist a physician or other healthcare providers in diagnosing the presence, non-presence, severity, and/or localization of diseases or conditions or in the treatment of said diseases or conditions.

The estimation or determined likelihood of the presence or non-presence of elevated LVEDP can supplant, augment, or replace other evaluation or measurement modalities for the assessment of elevated LVEDP. In some cases, a determination can take the form of a numerical score and related information.

A development system and environment are disclosed to develop the machine-learned models or classifiers of the clinical evaluation system. The feature sets, analytical and modeling framework of the development system and environment, and configuration of the clinical evaluation system can be applied, in parts and/or in combination with other features and model techniques, to the assessment or estimation of metrics associated with other pathologies or indication of one.

As used herein, the term "feature" (in the context of machine learning and pattern recognition and as used herein) generally refers to an individual measurable property or characteristic of a phenomenon being observed. A feature is defined by analysis and may be determined in groups in combination with other features from a common model or analytical framework.

As used herein, the term "metric" refers to an estimation or likelihood of the presence, non-presence, severity, and/or localization (where applicable) of one or more diseases, conditions, or indication(s) of either, in a physiological system or systems. Notably, the exemplified methods and systems can be used in certain embodiments described herein to acquire biophysical signals and/or to otherwise collect data from a patient and to evaluate those signals and/or data in signal processing and classifier operations to evaluate for a disease, condition, or indicator of one that can supplant, augment, or replace other evaluation modalities via one or more metrics. In some cases, a metric can take the form of a numerical score and related information.

In the context of cardiovascular and respiratory systems, examples of diseases and conditions to which such metrics can relate include, for example: (i) heart failure (e.g., left-side or right-side heart failure; heart failure with preserved ejection fraction (HFpEF)), (ii) coronary artery disease (CAD), (iii) various forms of pulmonary hypertension (PH) including without limitation pulmonary arterial hypertension (PAH), (iv) abnormal left ventricular ejection fraction (LVEF), and various other diseases or conditions. An example indicator of certain forms of heart failure is the presence or non-presence of elevated or abnormal left-ventricular end-diastolic pressure (LVEDP). An example indicator of certain forms of pulmonary hypertension is the presence or non-presence of elevated or abnormal mean pulmonary arterial pressure (mPAP).

As discussed above, the exemplified methods and systems facilitate analyses and modeling framework that can accurately and precisely estimate the presence or non-presence of elevated left-ventricular end-diastolic pressure using only non-invasive measurements.

In an aspect, a method is disclosed to non-invasively estimate presence of elevated left-ventricular end diastolic pressure (LVEDP) in a mammalian subject, the method comprising obtaining, by one or more processors, a first biophysical signal data set associated with a first photoplethysmographic signal and a second photoplethysmographic signal, wherein the first biophysical data set has been acquired over multiple cardiac cycles of the subject; obtaining, by the one or more processors, a second biophysical signal data set associated with a cardiac signal, wherein the second biophysical data set has been simultaneously acquired with the first biophysical signal data set over the multiple cardiac cycles; determining, by the one or more processors utilizing at least a portion of the first and second biophysical signal data sets, a plurality of values associated with a plurality of features; and determining, by the one or more processors, an estimated value for presence of elevated left-ventricular end diastolic pressure (LVEDP) using the plurality of values associated with the plurality of features assessing synchronicity between the cardiac signal and the photoplethysmographic signal and features associated with respective cardiac signal and the photoplethysmographic signal, wherein the estimated value (e.g., as an elevated LVEDP or HF score) for the presence of abnormal left-ventricular end diastolic pressure is outputted for use in a diagnosis of expected left heart failure (LHF) or to direct treatment of the expected left heart failure.

In some embodiments, the plurality of features include a feature set selected from the group consisting of one or more depolarization or repolarization wave propagation associated features; one or more depolarization wave propagation deviation associated features; one or more cycle variability associated features; one or more dynamical system associated features; one or more cardiac waveform topologic and variations associated features (e.g., linear features); one or more PPG waveform topologic and variations associated features (e.g., PPG linear features); one or more cardiac or PPG signal power spectral density associated features (e.g., cardiac/PPG visual features); one or more cardiac or PPG signal visual associated features; and one or more predictability features.

In some embodiments, the one or more depolarization or repolarization wave propagation associated features are configured to quantify a propagative characteristic (e.g., velocity, trajectory, orbital frequency (3D rotation rate), and/or planarity of the wave) of a ventricular depolarization (VD) wave or a ventricular repolarization (VR) wave defined in the cardiac signal in three-dimensional space.

In some embodiments, the one or more depolarization or repolarization wave propagation associated features are configured to quantify a propagative characteristic (e.g., velocity, trajectory, orbital frequency (3D rotation rate), and/or planarity of the wave) of a bandpass filtered ventricular depolarization (VD) wave or a ventricular repolarization (VR) wave defined in the cardiac signal in three-dimensional space (e.g., a QRS_max_Curvature_sub5 feature, which calculates a maximum curvature for the VD wave at a 5th frequency sub-band; a T_max_OrbitalFrequency_sub14 feature, which calculates the maximum orbital frequency for the VR wave at the 14th frequency sub-band).

In some embodiments, the one or more depolarization wave propagation deviation associated features are configured to quantify deviations, via evaluation of high-frequency and low-amplitude patterns, of a VD wave trajectory from a trajectory of a three-dimensional modeled VD wave, wherein the three-dimensional modeled VD wave is a representative VD wave below about 40 Hz (e.g., a maxCondDist feature, which calculates the maximum three-dimensional Euclidian distance between the model and original WD wave).

In some embodiments, the one or more cycle variability associated features are configured to quantify beat-to-beat variations of the cardiac signal in comparison of each respective beat to a determined template beat (e.g., CVscore_X feature, which calculates a distance between the cardiac signal and the template beat at a baseline waveform (e.g., signal region with no electrical activity) at orth1).

In some embodiments, the one or more dynamical system features (e.g., cardiac and PPG dynamical system analysis features) are configured to quantify dynamical characteristics (e.g., Lyapunov exponent, correlation dimension, entropy, mutual information, correlation, and nonlinear filtering) of the second biophysical data set (e.g., a LEX feature, which is a Lyapunov exponent of a biopotential channel orth1).

In some embodiments, the one or more cardiac waveform topologic and variations associated features (e.g., cardiac linear analysis features) are configured to quantify both cardiac measurements and variations (e.g., waveform amplitudes, durations, heart rate, and morphologies) of the second biophysical signal data set (e.g., an orth1_std_repolarization_Duration feature, which is a standard deviation of calculated repolarization duration for each beat in channel orth1).

In some embodiments, the one or more PPG waveform topologic and variations associated features (e.g., PPG linear analysis features) are configured to quantify both PPG measurements and variations (e.g., peak amplitudes, peak-to-peak distances, angles between points, and various ratios of the first photoplethysmographic signal and/or a second photoplethysmographic signal, a velocity photoplesymogram generated from the first photoplethysmographic signal and/or a second photoplethysmographic signal, and an acceleration photoplesymogram generated from the first photoplethysmographic signal and/or a second photoplethysmographic signal) of the first biophysical signal data set (e.g., a lowVPG_mean_peakDist feature, which calculates the peak-to-peak distance between the prominent peaks of red VPG for each beat and returns the mean distance).

In some embodiments, the one or more cardiac or PPG signal power spectral density associated features are configured to quantify a power spectrum and frequency content (e.g., power spectrum and coherence) of the first photoplethysmographic signal and a second photoplethysmographic signal (e.g., a cohKurt_PPG feature, which calculates the kurtosis of the coherence between the red and infrared PPG spectrum).

In some embodiments, the one or more cardiac or PPG signal power spectral density associated features are configured to quantify a power spectrum and frequency content (e.g., power spectrum, cross-spectral analysis, coherence) of the second biophysical signal data set (e.g., a coherence_sum_XY feature, which calculates the sum of the coherence between the orth1 and orth2 spectrum).

In some embodiments, the one or more cardiac or PPG visual associated features are configured to quantify geometric parameters of a three-dimensional phase space generated from the first or second biophysical data set (e.g., a lowerPPG_Circulation_PPGVPG feature, which calculates the rotation of the lower PPG loop in the PPG and VPG phase plane).

In some embodiments, the one or more predictability features are configured to quantify a predictability measure of the signal (e.g., predictability error and statistics of residues condensed from nonlinear filtering techniques), wherein the predictability measure measures an ability of a model trained on 75% of a signal to predict the remaining 25% (e.g., a StdResX feature, which is a standard deviation of residue from channel orth1).

In some embodiments, the one or more processors are located in a cloud platform.

In some embodiments, the one or more processors are located in a local computing device.

In some embodiments, the method further includes determining, by the one or more processors, via an outlier detection analysis of the first biophysical signal data set and the second biophysical signal data set, presence of outliers, wherein the outlier detection analysis comprises a machine learned module configured to detect arrythmia (i.e., sudden changes in heart rates) and/or incorrect lead configurations in the mammalian subject.

In some embodiments, the machine learned module is further configured to detect an anomalous waveform that is missing or has extra waveform elements (e.g., presence and/or absence of any of the depolarization and/or repolarization waves) in the first photoplethysmographic signal, the second photoplethysmographic signal, and/or the cardiac signal.

In some embodiments, the method further includes preprocessing, by the one or more processors, the second biophysical signal data set, wherein the preprocessing includes i) transient time removal operation, DC offset removal operation, and baseline wander removal operation.

In some embodiments, the method further includes determining, by the one or more processors, via signal quality assessment analysis of the first biophysical signal data set, a plurality of photoplethysmographic noise score of the first biophysical signal data set, including i) a first photoplethysmographic noise score associated with rapid changes in the first or second photoplethysmographic signals and ii) a second photoplethysmographic noise score associated with measurement saturation.

In some embodiments, the method further includes determining, by the one or more processors, via signal quality assessment analysis of the second biophysical signal data set, a plurality of biopotential noise score of the second biophysical signal data set, including a first biopotential noise score associated with biopotential powerline interference and a second biopotential noise score associated with bipotential high frequency noise.

In some embodiments, the step of determining the estimated value for presence of abnormal left-ventricular end diastolic pressure (LVEDP) values is determined by determining, by the one or more processors, a plurality of values for the plurality of features in two or more models, including a model selected from the group consisting of a linear model (e.g., Elastic Net), a decision tree model (XGB Classifier), a random forest model, a support vector machine model, a neural network model, and wherein the two or more models are combined (e.g., averaged) in an ensemble model that outputs the estimated value for the presence of abnormal left-ventricular end diastolic pressure (LVEDP).

In some embodiments, the ensemble model includes at least the two or more models and a model (e.g., a sigmoid model) associated with a body mass index (BMI) value of the mammalian subject.

In some embodiments, the plurality of features are selected from a pool of candidate features by a selection module.

In some embodiments, the selection module comprises a univariate feature assessment analysis that evaluates data sets (e.g., of a plurality of data sets) defined with respect to a positive pathology label associated with an elevated LVEDP and a negative pathology label associated with a normal LVEDP.

In some embodiments, the data sets are defined by a positive and negative pathology label (e.g., acquired from left heart catheterization (LHC)) selected from the group consisting of a LVEDP value greater than or equal to 20 mmHg and a LVEDP value less than or equal to 12 mmHg; and a LVEPD value greater than or equal to 25 mmHg and a LVEDP value less than or equal to 12 mmHg.

In some embodiments, the univariate feature assessment analysis is configured to determine a receiver-operating characteristic curve, a t-test, or a normalized mutual information analysis for presence of the elevated left-ventricular end diastolic pressure.

In some embodiments, the method further includes removing a feature from a plurality of candidate features having a high occurrence of extraction errors (e.g., prior to the univariate feature assessment analysis).

In some embodiments, the selection module comprises a cross-validation analysis (e.g., a stratified k-fold cross-validation analysis, e.g., 10-fold cross-validation analysis) for a set of trained models, wherein a set of data set is randomly sampled (e.g., 80%) as a training data set and a remainder is used as a validation data set in a feature permutation importance analysis.

In some embodiments, the feature permutation importance analysis quantifies a utility of a feature in combination with all other assessed features.

In some embodiments, the plurality of features are configured in a machine-learned model.

In some embodiments, the machine-learned model is trained using hyperparameters selected from a group of hyperparameters that have been evaluated in a hyperparameter sensitivity analysis.

In another aspect, a method is disclosed to reject an acquired biophysical signal data set as an outlier signal during an analysis to non-invasively estimate presence of elevated left-ventricular end diastolic pressure (LVEDP) in a mammalian subject, the method comprising obtaining, by one or more processors, a first biophysical signal data set associated with a first photoplethysmographic signal and a second photoplethysmographic signal, wherein the first biophysical data set has been acquired over multiple cardiac cycles of the subject; obtaining, by the one or more processors, a second biophysical signal data set associated with a cardiac signal, wherein the second biophysical data set has been simultaneously acquired with the first biophysical signal data set over the multiple cardiac cycles; determining, by the one or more processors and/or remotely by one or more cloud-based services or systems, via an outlier detection analysis of the first biophysical signal data set and the second biophysical signal data set, presence of outliers, wherein the outlier detection analysis comprises a machine learned model (e.g., forest model) configured to at least one of i) sudden changes in heart rates in the mammalian subject or ii) an anomalous waveform that is missing or has extra waveform elements; and rejecting, by the one or more processors and/or remotely by one or more cloud-based services or systems, the first and second biophysical signal data sets based on the outlier detection analysis, wherein the rejection generates a notification to be presented at i) measurement equipment used to acquire the first or second biophysical signal data set or ii) a remote terminal.

In some embodiments, the method further includes generating, by the one or more processors, a notification of at least one of the first and second biophysical signal data set being an outlier dataset based on the determination, wherein a non-rejected first biophysical signal data set and the second biophysical signal data set are used to estimate one or more values associated with a presence of an expected disease state or condition, and wherein the value is subsequently outputted for use in a diagnosis of the expected disease state or condition or to direct treatment of the expected disease state or condition.

In some embodiments, the machine learned model is configured using an unsupervised learning algorithm (e.g., Isolation Forest) configured to evaluate randomly selected features of the plurality of features and to evaluate a selected feature using random splitting points between maximum and minimum values of a set of features.

In some embodiments, the plurality of features include a feature set selected from the group consisting of one or more depolarization or repolarization wave propagation associated features; one or more depolarization wave propagation deviation associated features; one or more cycle variability associated features; one or more dynamical system associated features; one or more cardiac waveform topologic and variations associated features (e.g., linear features); one or more PPG waveform topologic and variations associated features (e.g., PPG linear features); one or more cardiac or PPG signal power spectral density associated features (e.g., cardiac/PPG visual features); one or more cardiac or PPG signal visual associated features; and one or more predictability features.

In some embodiments, the method further includes determining, by the one or more processors and/or remotely by one or more cloud-based services or systems, via a signal quality or cycle variability analysis of the acquired first and second biophysical signal data sets; and rejecting, by the one or more processors and/or remotely by one or more cloud-based services or systems, the first and second biophysical signal data sets based on the signal quality or cycle variability analysis, wherein the rejection generates a second notification to be presented at i) measurement equipment used to acquire the first or second biophysical signal data set or ii) a remote terminal.

In another aspect, a method is disclosed to configure a model to non-invasively estimate presence of a metric associated with an abnormal condition or disease state, the method comprising selecting, via a feature selection operation (e.g., univariate feature selection), a plurality of features from a plurality of candidate feature sets; training the plurality of selected features in one or more models, to produce a plurality of candidate models, wherein the one or more models include a model selected from the group consisting of a linear model (e.g., Elastic Net), a decision tree model (XGB Classifier), a random forest model, a support vector machine model, a neural network model, and wherein each of the one or more models is configured to output an estimated value associated with a presence of an expected disease state or condition or condition, wherein the estimated value is subsequently outputted for use in a diagnosis of the expected disease state or condition or to direct treatment of the expected disease state or condition; performing a stratified k-fold cross-validation operation of the plurality of trained candidate models; and validating the cross-validated models.

In some embodiments, the feature selection operation includes a univariate feature assessment analysis that evaluates data sets (e.g., of a plurality of data sets) defined with respect to a positive pathology label associated with the expected disease state or condition and a negative pathology label associated with the expected disease state or condition.

In some embodiments, the method further includes performing a hyperparameter sensitivity analysis to determine stability values for hypermeters of the plurality of trained candidate models; and removing a trained candidate model of the plurality of trained candidate models having determined unstable stability values.

In some embodiments, the data sets are defined by a positive and negative pathology label selected from the group consisting of a LVEDP value greater than or equal to 20 mmHg and a LVEDP value less than or equal to 12 mmHg; and a LVEPD value greater than or equal to 25 mmHg and a LVEDP value less than or equal to 12 mmHg.

In some embodiments, the data sets are defined by a positive and negative pathology label associated with the presence or non-presence of significant coronary arterial disease (CAD).

In some embodiments, the data sets are defined by a positive and negative pathology label associated with the presence or non-presence of pulmonary hypertension.

In some embodiments, the expected disease or condition can be diagnosed based on assessed indication and/or estimate of presence, non-presence, and/or severity of elevated or abnormal left ventricular end-diastolic pressure (LVEDP).

In some embodiments, the expected disease state or condition includes left ventricular heart failure or left-sided heart failure.

In some embodiments, the expected disease state or condition includes coronary artery disease.

In some embodiments, the expected disease state or condition includes pulmonary hypertension.

In some embodiments, the expected disease state or condition includes pulmonary arterial hypertension.

In some embodiments, the expected disease state or condition includes pulmonary hypertension due to left heart disease.

In some embodiments, the expected disease state or condition includes rare disorders that lead to pulmonary hypertension.

In some embodiments, the expected disease state or condition includes right ventricular heart failure or right-sided heart failure.

In some embodiments, the expected disease state or condition includes systolic heart failure.

In some embodiments, the expected disease state or condition includes diastolic heart failure.

In some embodiments, the disease state or condition includes ischemic heart disease.

In some embodiments, the disease state or condition includes arrhythmia.

In another aspect, a system (e.g., cloud platform or local computing platform) is disclosed comprising one or more processors; and one or more memory having instructions respectively stored thereon, wherein execution of the instructions by the one or more processors cause the one or more processors to perform any one of the above-discussed method.

In another aspect, a non-transitory computer readable medium is disclosed comprising instructions stored thereon, wherein execution of the instructions by one or more processors cause the one or more processors to perform any one of the above-discussed method.

BRIEF DESCRIPTION OF THE DRAWINGS

The accompanying drawings, which are incorporated in and constitute a part of this specification, illustrate embodiments and, together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 3A shows an example method to estimate or determine the likelihood of elevated LVEDP from non-invasively acquired biophysical signals.

FIG. 3B shows an example of sets of feature modules that can be used in the LVEDP assessment operation and workflow.

DETAILED DESCRIPTION

Figure 1:
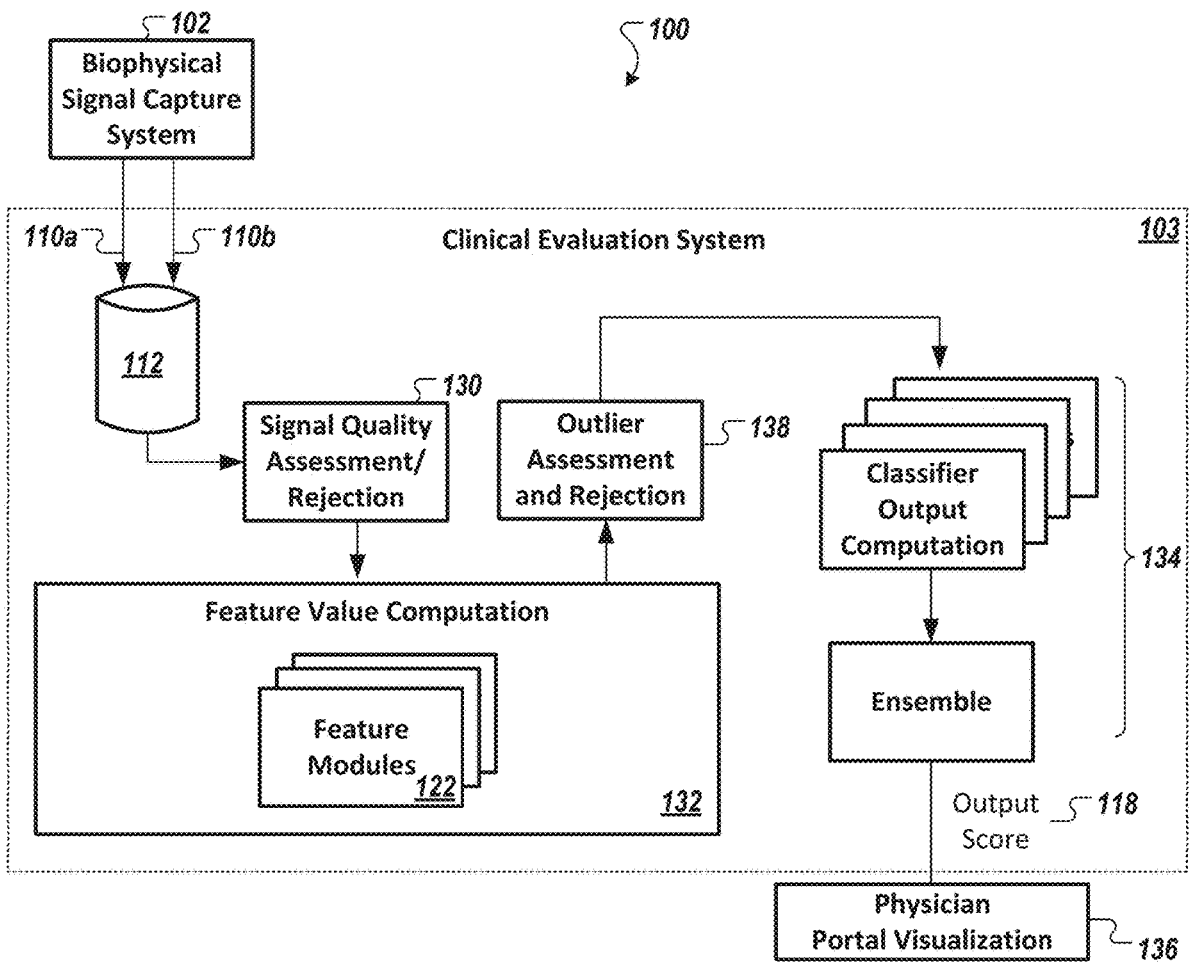
FIG. 1 shows a schematic diagram of the operation and workflow of an analytical engine or analyzer of a clinical evaluation system that can non-invasively estimate or determine a likelihood of the presence, non-presence, severity, and/or localization of a disease state, medical condition, or an indication of either in a patient.

Each and every feature described herein, and each and every combination of two or more of such features, is included within the scope of the present invention provided that the features included in such a combination are not mutually inconsistent.

While the present disclosure is directed to the practical assessment of biophysical signals, e.g., raw or pre-processed photoplethysmographic signals, biopotential/cardiac signals, etc., in the diagnosis, tracking, and treatment of cardiac-related pathologies and conditions, such assessment can be applied to the diagnosis, tracking, and treatment (including without limitation surgical, minimally invasive, lifestyle, nutritional, and/or pharmacologic treatment, etc.) of any pathologies or conditions in which a biophysical signal is involved in any relevant system of a living body. The assessment may be used in the controls of medical equipment or wearable devices or in monitoring applications (e.g., to report respiration rate or associated waveforms generated using the biophysical signals as disclosed therein).

The terms "subject" and "patient" as used herein are generally used interchangeably to refer to those who had undergone analysis performed by the exemplary systems and methods.

The term "cardiac signal" as used herein refers to one or more signals directly or indirectly associated with the structure, function, and/or activity of the cardiovascular system— including aspects of that signal's electrical/electrochemical conduction—that, e.g., cause contraction of the myocardium. A cardiac signal may include, in some embodiments, biopotential signals or electrocardiographic signals, e.g., those acquired via an electrocardiogram (ECG), the cardiac and photoplethysmographic waveform or signal capture or recording instrument later described herein, or other modalities.

The term "biophysical signal" as used herein includes but is not limited to one or more cardiac signal(s), neurological signal(s), ballistocardiographic signal(s), and/or photoplethysmographic signal(s), but it also encompasses more broadly any physiological signal from which information may be obtained. Not intending to be limited by example, one may classify biophysical signals into types or categories that can include, for example, electrical (e.g., certain cardiac and neurological system-related signals that can be observed, identified, and/or quantified by techniques such as the measurement of voltage/potential (e.g., biopotential), impedance, resistivity, conductivity, current, etc. in various domains such as time and/or frequency), magnetic, electromagnetic, optical (e.g., signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g., signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), one or more organ system(s) (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements, and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic, and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light, and other ways of actively interrogating the body tissue that does not involve ionizing energy or radiation (e.g., X-ray). An active biophysical signal acquisition may involve excitation-emission spectroscopy (including, for example, excitation-emission fluorescence). The active biophysical signal acquisition may also involve transmitting ionizing energy or radiation (e.g., X-ray) (also referred to as "ionizing biophysical signal") to the body tissue. Passive and active biophysical signal acquisition means can be performed in conjunction with invasive procedures (e.g., via surgery or invasive radiologic intervention protocols) or non-invasively (e.g., via imaging, ablation, heart contraction regulation (e.g., via pacemakers), catheterization, etc.).

The term "photoplethysmographic signal" as used herein refers to one or more signals or waveforms acquired from optical sensors that correspond to measured changes in light absorption by oxygenated and deoxygenated hemoglobin, such as light having wavelengths in the red and infrared spectra. Photoplethysmographic signal(s), in some embodiments, include a raw signal(s) acquired via a pulse oximeter or a photoplethysmogram (PPG). In some embodiments, photoplethysmographic signal(s) are acquired from off-the-shelf, custom, and/or dedicated equipment or circuitries that are configured to acquire such signal waveforms for the purpose of monitoring health and/or diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near-infrared, blue and green may be used in different combinations, depending on the type and/or mode of PPG being employed.

The term "ballistocardiographic signal," as used herein, refers to a signal or group of signals that generally reflect the flow of blood through the entire body that may be observed through vibration, acoustic, movement, or orientation. In some embodiments, ballistocardiographic signals are acquired by wearable devices, such as vibration, acoustic, movement, or orientation-based seismocardiogram (SCG) sensors, which can measure the body's vibrations or orientation as recorded by sensors mounted close to the heart. Seismocardiogram sensors are generally used to acquire "seismocardiogram," which is used interchangeably with the term "ballistocardiogram" herein. In other embodiments, ballistocardiographic signals may be acquired by external equipment, e.g., bed or surface-based equipment that measures phenomena such as a change in body weight as blood moves back and forth in the longitudinal direction between the head and feet. In such embodiments, the volume of blood in each location may change dynamically and be reflected in the weight measured at each location on the bed as well as the rate of change of that weight.

In addition, the methods and systems described in the various embodiments herein are not so limited and may be utilized in any context of another physiological system or systems, organs, tissue, cells, etc., of a living body. By way of example only, two biophysical signal types that may be useful in the cardiovascular context include cardiac/biopotential signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography. In another example, the two biophysical signal types can be further augmented by ballistocardiographic techniques.

FIG. 1 shows a schematic diagram of the operation and workflow of an analytical engine or analyzer (e.g., 806, 814—see FIG. 8) of a clinical evaluation system 103 that can non-invasively estimate or determine a likelihood of the presence, non-presence, severity, and/or localization of a disease state, medical condition, or an indication of either in a patient. The analytical engines or analyzers include the operation and workflow for signal quality assessment and rejection (130), feature value computation (132), classifier output and ensemble computation and (134), physician portal visualization (136), and outlier assessment and rejection (138).

The analytical engine or analyzer is configured to non-invasively compute features or parameters to generate, via a classifier (e.g., machine-learned classifier), one or more metrics associated with the physiological state of a patient in accordance with an illustrative embodiment, e.g., to assist a healthcare provider in the diagnosis and/or treatment of cardiac- and cardiopulmonary-related pathologies and medical conditions, or an indicator of one. Examples include significant coronary artery disease (CAD), one or more forms of heart failure such as, e.g., heart failure with preserved ejection fraction (HFpEF), congestive heart failure, various forms of arrhythmia, valve failure, various forms of pulmonary hypertension, among various other disease and conditions disclosed herein.

In addition, there exist possible indicators of a disease or condition, such as an elevated or abnormal left ventricular end-diastolic pressure (LVEDP) value as it relates to some forms of heart failure, abnormal left ventricular ejection fraction (LVEF) values as they relate to some forms of heart failure or an elevated mean pulmonary arterial pressure (mPAP) value as it relates to pulmonary hypertension and/or pulmonary arterial hypertension. Indicators of the likelihood that such indicators are abnormal/elevated or normal, such as those provided by the example analysis and classifiers described herein, can help a healthcare provider assess or diagnose that the patient has or does not have a given disease or condition. In addition to these metrics associated with a disease state of condition, other measurements and factors may be employed by a healthcare professional in making a diagnosis, such as the results of a physical examination and/or other tests, the patient's medical history, current medications, etc. The estimation of the presence or non-presence of a disease state or medical condition can include the indication (or a metric of estimation that is used in the diagnosis) for such disease.

In FIG. 1, Clinical evaluation system 103 operates with a non-invasive biophysical signal recorder or capture system 102. The clinical evaluation system 103 may be implemented in cloud/remote infrastructure or in a local system.

Figure 2:
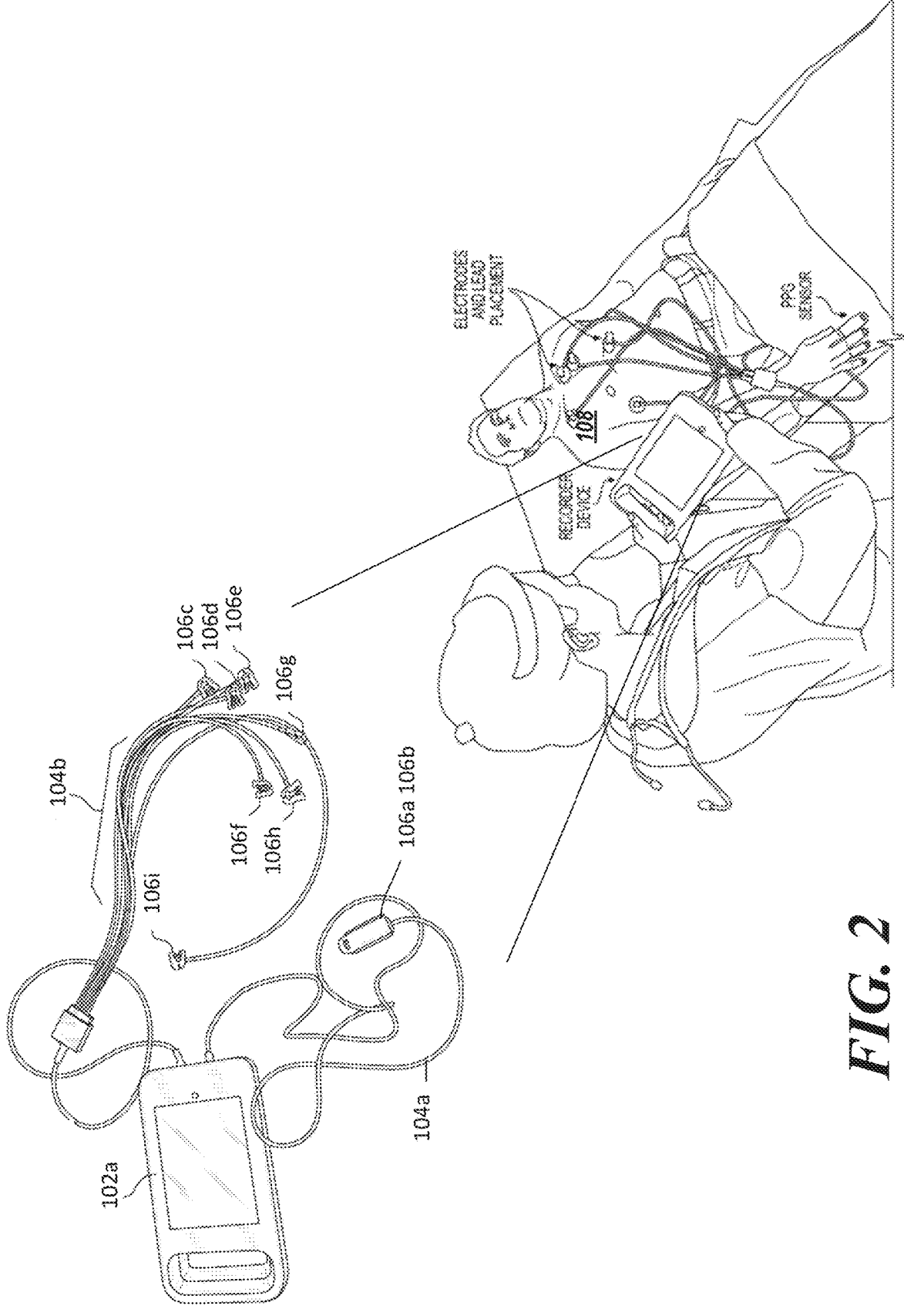
FIG. 2 shows an example biophysical signal capture system or component and its use in non-invasively collecting biophysical signals of a patient in a clinical setting in accordance with an illustrative embodiment.

Biophysical signal capture system 102 (also referred to as a biophysical signal recorder system) is configured to, e.g., acquire, process, and store (and in certain implementations, transmit) synchronously acquired patient's electrical and hemodynamic signals as one or more types of biophysical signals 104 (not shown—see FIG. 2). In the example of FIG. 1, Biophysical signal capture system 102 is configured to synchronously capture two types of biophysical signals shown as first biophysical signals (e.g., synchronously acquired to other first biophysical signals) and second bio-physical signals (e.g., synchronously acquired to the other biophysical signals) acquired from measurement probes 106 (e.g., not shown—see probes 106a and 106b, e.g., compris-ing hemodynamic sensors for hemodynamic signals 104a, and probes 106c-106h comprising leads for electrical/car-diac signals 104b in FIG. 2). The probes 106a-h are placed on, e.g., by being adhered to or placed next to, a surface tissue of a patient 108 (shown at patient locations 108a and 108b). The patient is preferably a human patient, but it can be any mammalian patient. The acquired raw biophysical signals (e.g., 106a and 106b) together form a biophysical-signal data set 110 (shown in FIG. 1 as a first biophysical-signal data set 110a and a second biophysical-signal data set 110b, respectively) that may be stored, e.g., as a single file, preferably, that is identifiable by a recording/signal captured number and/or by a patient's name and medical record number.

In the FIG. 1 embodiment, the first biophysical-signal data set 110a comprises a set of raw photoplethysmographic, or hemodynamic, signal(s) associated with measured changes in light absorption of oxygenated and/or deoxygen-ated hemoglobin from the patient at location 108a, and the second biophysical-signal data set 110b comprises a set of raw cardiac or biopotential signal(s) associated with elec-trical signals of the heart. Though in FIG. 1, raw photopl-ethysmographic or hemodynamic signal(s) are shown to be acquired at a patient's finger, the signals may be alterna-tively acquired at the patient's toe, wrist, forehead, earlobe, neck, etc. Similarly, although the cardiac or biopotential signal(s) are shown to be acquired via three sets of orthogo-nal leads, other lead configurations may be used (e.g., 11 lead configuration, 12 lead configuration, etc.).

The biophysical signal capture system 102 preferably acquires biophysical signals via non-invasive means or component(s). In alternative embodiments, invasive or mini-mally-invasively means or component(s) may be used to supplement or as substitutes for the non-invasive means (e.g., implanted pressure sensors, chemical sensors, accel-erometers, and the like). In still further alternative embodi-ments, non-invasive and non-contact probes or sensors capable of collecting biophysical signals may be used to supplement or as substitutes for the non-invasive and/or invasive/minimally invasive means, in any combination (e.g., passive thermometers, scanners, cameras, x-ray, mag-netic, or other means of non-contact or contact energy data collection system as discussed herein). Subsequent to signal acquisitions and recording, biophysical signal capture sys-tem 102 then provides, e.g., sending over a wireless or wired communication system and/or a network, the acquired bio-physical-signal data sets 110a, 110b (or a data set derived or processed therefrom, e.g., filtered or pre-processed data) to a data repository 112 (e.g., a cloud-based storage area network) of the clinical evaluation system 103. In some embodiments, the acquired biophysical-signal data sets 110a, 110b are sent directly to the clinical evaluation system 103 for analysis or are uploaded to a data repository 112 through a secure clinician's portal. The data sets may be separately sent in multiple files or in a single data file. In other embodiments, the acquired biophysical-signal data sets 110a, 110b are analyzed by a clinical evaluation system executing on a local network computing device that can provide the results to a cloud/remote server.

Biophysical signal capture system 102 is configured with circuitries and computing hardware, software, firmware, middleware, etc., in some embodiments, to acquire, store, transmit, and optionally process both the captured biophysi-cal signals to generate the biophysical-signal data set 110. An example biophysical signal capture system 102 and the acquired biophysical-signal set data 110 are described in U.S. Pat. No. 10,542,898, entitled "Method and Apparatus for Wide-Band Phase Gradient Signal Acquisition," or U.S. Patent Publication No. 2018/0249960, entitled "Method and Apparatus for Wide-Band Phase Gradient Signal Acquisi-tion," each of which is hereby incorporated by reference herein in its entirety.

In some embodiments, biophysical signal capture system 102 includes two or more signal acquisition components, including a first signal acquisition component (not shown) to acquire the first biophysical signals (e.g., photoplethysmo-graphic signals) and includes a second signal acquisition component (not shown) to acquire the second biophysical signals (e.g., cardiac signals). In some embodiments, the electrical signals are acquired at a multi-kilohertz rate for a few minutes, e.g., between 1 kHz and 10 kHz. In other embodiments, the electrical signals are acquired between 10 kHz and 100 kHz. The hemodynamic signals may be acquired, e.g., between 100 Hz and 1 kHz.

Biophysical signal capture system 102 may include one or more other signal acquisition components (e.g., sensors such as mechano-acoustic, ballistographic, ballistocardiographic, etc.) for acquiring signals. In other embodiments of the signal capture system 102, a signal acquisition component comprises conventional electrocardiogram (ECG/EKG) equipment (e.g., Holter device, 12 lead ECG, etc.).

Signal quality assessment/rejection (130). Analytical engine or analyzer (808, 814—see FIG. 8) assesses (130) the quality of the acquired biophysical-signal data set while the analysis pipeline is executing. The results of the assessment (e.g., pass/fail) may be performed, e.g., in a cloud-connected or network clinical evaluation system or a local version of one, and are immediately returned to the signal capture system's user interface for reading by the user. Acquired signal data that meet the signal quality requirements are deemed acceptable (i.e., "pass") and may be further pro-cessed and subjected to analysis for the presence of metrics associated with the pathology or medical condition (e.g., elevated LVEDP, CAD, PH/PAH, abnormal LVEF, HFpEF) by the analytical engine or analyzer. Acquired signals deemed unacceptable are rejected (e.g., "fail"), and a noti-fication is immediately sent to the user to inform the user to immediately obtain additional signals from the patient 108 (see FIG. 2).

The analytical engine or analyzer can perform two sets of initial assessments for signal quality (130), one for the electrical signals and one for the hemodynamic signals. Operations (130) can confirm that the electrical signals (e.g., of the cardiac/biopotential signal data set 110b) are of sufficient length, lack high-frequency noise (e.g., above 170 Hz), and lack power line noise from the environment (e.g., 50 Hz or 60 Hz). An assessment of the hemodynamic signals can confirm (i) the percentage of outliers in the hemody-namic data set is below a pre-defined threshold and (ii) the percentage or maximum duration that the signals of the hemodynamic data set is railed, clipped, or saturated below a pre-defined threshold. Additional examples of signal quality assessments may be found in U.S. patent application Ser. No. 17/132,869, filed Dec. 23, 2020, entitled "Method and System for Signal Quality Assessment Using Heart Cycle Variability," and U.S. Patent Publication no. 2020/0205739, entitled "Method and System for Automated Quantification of Signal Quality," and PCT Publication no. WO2020/136570, entitled "Method and System for Automated Quantification of Signal Quality," each of which is hereby incorporated by reference herein in its entirety.

Feature Value Computation (132). Analytical engine or analyzer (e.g., 806, 814—see FIG. 8) can compute (132) feature output values for a plurality of features modules 122 associated with a given clinical application. In the example of the LVEDP algorithm, the analytical engine or analyzer can determine, in some embodiments, a total of 446 feature outputs belonging to multiple feature families implemented in Modules 122. The list of the features in the LVEDP algorithm and description are provided in Table 1, later discussed herein.

Modules 122 may evaluate any number of features, including features that quantify waveform morphologies of biophysical signals or signals derived from the biophysical signals (e.g., morphologies of PPG signals and VPG/APG signals generated from the PPG signals and/or cardiac/biopotential signals). Modules 122 may evaluate features that quantify the spectral power of waveform regions in the biophysical signals. Modules 122 may evaluate features that quantify the spectral power of waveform regions of a cardiac/biopotential signal (e.g., ventricular depolarization, ventricular repolarization, and atrial depolarization regions) using wavelet analysis. Modules 122 may evaluate features that quantify propagative characteristics or visual topologic characteristics (e.g., velocity, trajectory, orbital frequency, planarity, vector length among registration points) in three-dimensional phase space of biophysical signals or regions in the biophysical signals. Modules 122 may evaluate features that quantify beat-to-beat variations (cycle variability) in a biophysical signal. Modules 122 may evaluate features that quantify synchronicity using Poincare plots among registration points in biophysical signals. Modules 122 may evaluate features that quantify dynamical characteristics of biophysical signals by way of dynamical system analysis. Modules 122 may evaluate features that quantify the power spectrum and frequency content of biophysical signals. Modules 122 may evaluate features that quantify the predictability of the signal. Modules 122 may evaluate features that assess biophysical signals in various phase space associated analyses (e.g., Phase Space Tomography), phase space models, phase space volumetric models.

Analytical engine or analyzer (e.g., 806, 814—see FIG. 8) may perform pre-processing and/or pre-conditioning operations (e.g., 818—see FIG. 8) to the signals. In some embodiments, the analytical engine or analyzer can process the acquired signals (e.g., cardiac signals) to remove transient time (e.g., the first 5 seconds, 10 seconds 20 seconds, 30 seconds, 31 seconds, 45 seconds, 1 minute, etc.) of the signal and omit or remove them from subsequent analysis, e.g., in case such portion of the signal was obtained while any initial motion of the patient at the start of the signal acquisition procedure may have occurred and/or while the electrode or sensor contact settles or initially shifts. The analytical engine or analyzer may remove the direct current (DC) offset of the acquired signal, e.g., by subtracting the acquired signal (e.g., cardiac signals) from its mean for each acquired channel. The analytical engine or analyzer may remove an assessed baseline wander, e.g., by subtracting the acquired signal (e.g., cardiac signals) from its low-frequency baseline. In some embodiments, the baseline is generated by a reconstruction operation that uses a stationary wavelet transform (e.g., Daubechies wavelet with a number of vanishing moments, e.g., 8 moments) that preserves its coefficients at the lowest frequency.

Outlier Assessment and Rejection Detection (138). Following the computation of the feature value outputs (in process 132) and prior to their application to the classifier models (in process 134, Analytical engine or analyzer (e.g., 806, 814—see FIG. 8) can perform outlier analysis (shown in process 138) of the feature value outputs. Outliers are signals (e.g., cardiac and/or photoplethysmographic signals) that are unlikely to be observed or expected to be observed in the trained dataset. It is desirable to remove outliers because, by the definition of an outlier as unlikely to be observed, the training or assessment system has very limited exposure to such signals, and therefore the possibility of prediction error is higher on an outlier signal as compared to a non-outlier signal.

The outlier detection module assesses for outliers that present themselves within sparse clusters at isolated regions that are out of distribution from the rest of the observations. Process 138 can reduce the risk that outlier signals are inappropriately applied to the classifier models and produce inaccurate estimates that would otherwise be viewed by the patient or healthcare provider.

Outlier analysis evaluation process 138 can execute an outlier detection module (ODM) to identify and exclude anomalous acquired biophysical signals to prevent the generation of a final score that has a higher likelihood of error due to outlier signals. Outlier analysis evaluation process 138 can employ an unsupervised learning algorithm (e.g., Isolation Forest or other decision tree-based methods) for anomaly detection. Outlier analysis evaluation process 138 can isolate samples through the selection of random features and randomly splitting points between the maximum and minimum values of that feature. In the example of an isolation forest, operation 138 can employ the natural tendency for outliers to separate from the rest of the observations with a few steps through the trees (shorter average pathway). The 'forest' algorithm, in some embodiments, is configured to generate a collection of decision trees and to make a final decision based on all the trees within the forest.

Two categories of anomalous signals may be evaluated, among others, by the outlier detection model (ODM), including arrhythmic data sets and inverted lead data sets. Arrhythmic data sets, in some embodiments, are labeled based on one or more indicators, including (i) sudden changes in heart rates or (ii) missing or extra waveforms. Sudden changes in heart rate may be defined as a burst of fast cycles (paroxysmal tachycardia) or a sudden change from one reasonable heart rate to another. An example includes a determined change from 72 bpm to 48 bpm, which is a 2:1 change in the AV node block signal. Missing or extra waveforms may be defined as a presence and/or absence of any of the depolarization and/or repolarization waves, e.g., ventricular or atrial depolarization waveforms (also referred to as a QRS wave or P-waves). Inverted leads (e.g., as caused by misplacement of the electrodes on the torso) can be a clinical study protocol deviation in the collection of the data set that can generate anomalous signals to which hyperparameters of ODM can be tuned to encourage its detection.

In an example, the ODM operator can be trained using an ensemble of isolation forests (e.g., 50 models) on a data set consisting of 1000+ signals, while hyperparameter tuning was performed on a labeled test set consisting of signals with two categories of arrhythmia and inverted leads. To enhance the ODM robustness to the noise in the dataset, models can be trained each on the 80% of randomly selected samples from the training data and the rest used for testing. The ODM prediction may be based on ensemble voting (the arithmetic mean of the outlier scores of each model). During the hyperparameters tuning, the ODM operator is evaluated to identify all the labeled anomalous signals in a test set with an acceptable outlier detection rate (ODR) generalization. The results can be confirmed using a hold-out validation set. Additional examples and descriptions of other isolation forest methods are described in Liu, Fei Tony, Ting, Kai Ming and Zhou, Zhi-Hua. "Isolation forest." Data Mining, 2008. ICDM'08. Eighth IEEE International Conference (2008), which is incorporated by reference herein in its entirety.

Classifier Output Computation (1334). Analytical engine or analyzer (e.g., 806, 814—see FIG. 1) then uses the calculated feature outputs in classifier models (e.g., machine-learned classifier models) to generate a set of model scores. Classifier models may include transfer functions, look-up tables, models, or operators developed based on algorithms such as but not limited to decision trees, random forests, neural networks, linear models, Gaussian processes, nearest neighbor, SVMs, Naïve Bayes, etc. The analytical engine or analyzer can join the set of model scores in an ensemble of the constituent models, which, in some embodiments, averages the output of the classifier models as shown in Equation 1.

$$\text{Ensemble estimation} = \frac{Model_1 + Model_2 + \ldots + Model_n}{n} \quad \text{(Equation 1)}$$

In some embodiments, classifier models may include models that are developed based on ML techniques described in U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

In the example of the LVEDP algorithm, thirteen (13) machine-learned classifier models are each calculated using the calculated feature outputs. The 13 classifier models include four ElasticNet machine-learned classifier models [9], four RandomForestClassifier machine-learned classifier models [10], and five extreme gradient boosting (XGB) classifier models [11]. In some embodiments, the patient's metadata information, such as age, gender, and BMI value, may be used. The output of the ensemble estimation may be a continuous score. The score may be shifted to a threshold value of zero by subtracting the threshold value for presentation within the web portal. The threshold value may be selected as a trade-off between sensitivity and specificity. The threshold may be defined within the algorithm and used as the determination point for test positive (e.g., "Likely Elevated LVEDP") and test negative (e.g., "Not Likely Elevated LVEDP") condition.

In some embodiments, the analytical engine or analyzer can fuse the set of model scores with a body mass index-based adjustment or an adjustment based on age or gender.

For example, the analytical engine or analyzer can average the model estimation with a sigmoid function of the patient BMI having the form $$\text{sigmoid } (x) = \frac{1}{1 + e^{-x}}.$$

Physician Portal Visualization (136). The patient's report may include a visualization 136 of the acquired patient data and signals and the results (e.g., shown as an output score 118 in an example) of the disease analyses. The analyses may be presented in multiple sections within the report, including a section that shows the score, a section that shows the score with respect to a positive indication population group and a negative indication group, and a section that shows the specificity and sensitivity performance of the score. A healthcare provider, e.g., a physician, can review the report and interpret it to provide a diagnosis of the disease or to generate a treatment plan. The healthcare portal may list a report for a patient if a given patient's acquired signal data set meets the signal quality standard. The report may indicate a disease-specific result, e.g., (i) estimation of the presence or non-presence of elevated indication of a disease or condition (e.g., elevated LVEDP or mPAP or other indications discussed herein) or (ii) presence, non-presence, severity, or localization of a disease or medical condition (e.g., CAD, PH, PAH, or other disease or conditions as described herein).

The output report may be via a wearable device, a handheld device, or a medical diagnostic equipment (e.g., pulse oximeter system, wearable health monitoring systems). In some embodiments, the output may be via a point of care monitoring, such as a mobile cart or cart trolley. In some embodiments, the outputs may be used in resuscitation systems, cardiac or pulmonary stress test equipment, pacemakers, etc., in which frequency spectral information is desired.

Example Biophysical Signal Acquisition

FIG. 2 shows a biophysical signal capture system 102 (shown as 102*a*) and its use in non-invasively collecting biophysical signals of a patient in a clinical setting in accordance with an illustrative embodiment. In FIG. 2, the biophysical signal capture system 102*a* is configured to capture two types of biophysical signals from patient 108 while the patient is at rest. Biophysical signal capture system 102*a* synchronously acquires the patient's (i) electrical signals (e.g., cardiac signals corresponding to the second biophysical-signal data set 110*b*) from the torso using orthogonally placed sensors (106*c*-106*h*; 106*i* is a common-mode reference lead) and (ii) hemodynamic signals (e.g., PPG signals corresponding to the first biophysical-signal data set 110*a*) from the finger using a photoplethysmographic sensor (e.g., collecting signals 106*a*, 106*b*).

As shown in FIG. 2, the electrical and hemodynamic signals (e.g., 104*a*, 104*b*) are passively collected via commercially available sensors applied to the patient's skin. The signals may be acquired beneficially without patient exposure to ionizing radiation or radiological contrast agents and without patient exercise or the use of pharmacologic stressors. The biophysical signal capture system 102*a* can be used in any setting conducive for a healthcare professional, such as a technician or nurse, to acquire the requisite data and where a cellular signal or Wi-Fi connection can be established.

The electrical signals (e.g., corresponding to the second biophysical signal data set 110b) are collected using three orthogonally paired surface electrodes arranged across the patient's chest and back along with a reference lead. The electrical signals are acquired, in some embodiments, using a low-pass anti-aliasing filter (e.g., 2 kHz) at a multi-kilohertz rate (e.g., 8 thousand samples per second for each of the six channels) for a few minutes (e.g., 215 seconds). In alternative embodiments, the biophysical signals may be continuously/intermittently acquired for monitoring, and portions of the acquired signals are used for analysis. The hemodynamic signals (e.g., corresponding to the first biophysical signal data set 110a) are collected using a photoplethysmographic sensor placed on a finger. The photoabsorption of red light (e.g., any wavelengths between 600-750 nm) and infrared light (e.g., any wavelengths between 850-950 nm) are recorded, in some embodiments, at a rate of 500 samples per second over the same period. The biophysical signal capture system 102a may include a common mode drive that reduces common-mode environmental noise in the signal. The photoplethysmographic and cardiac signals were simultaneously acquired for each patient. Jitter (inter-modality jitter) in the data may be less than about 10 microseconds (μs). Jitter among the cardiac signal channels may be less than 10 microseconds, e.g., around ten femtoseconds (fs).

A signal data package containing the patient metadata and signal data may be compiled at the completion of the signal acquisition procedure. This data package may be encrypted before the biophysical signal capture system 102a transfers to the data repository 112. In some embodiments, the data package is transferred to the clinical evaluation system (e.g., 103). The transfer is initiated, in some embodiments, following the completion of the signal acquisition procedure without any user intervention. The data repository 112 is hosted, in some embodiments, on a cloud storage service that can provide secure, redundant, cloud-based storage for the patient's data packages, e.g., Amazon Simple Storage Service (i.e., "Amazon S3"). The biophysical signal capture system 102a also provides an interface for the practitioner to receive notification of an improper signal acquisition to alert the practitioner to immediately acquire additional data from the patient.

Example Method of Operation

FIG. 3 shows an example method 300 for non-invasively determining an estimation for the presence of elevated LVEDP. Method 300 may additionally determine an estimation for the non-presence of elevated LVEDP to assess in combination with the positive determination. Method 300 includes the step of obtaining (302) a first biophysical signal data set associated with a first photoplethysmographic signal and a second photoplethysmographic signal, e.g., as described in relation to FIGS. 1 and 2 and other examples described herein. In some embodiments, the acquired biophysical signal data set is transmitted for remote storage and analysis. In other embodiments, the acquired biophysical signal data set is stored and analyzed locally. The first biophysical data set may have been acquired over multiple cardiac cycles of the patient.

Method 300 further includes the step of obtaining (304) a second biophysical signal data set associated with a cardiac signal, wherein the second biophysical data set has been simultaneously acquired with the first biophysical signal data set over the multiple cardiac cycles.

Method 300 further includes the step of determining (306), utilizing at least a portion of the first and second biophysical signal data sets, a plurality of values associated with a plurality of features. Method 300 further includes the step of determining (308) an estimate in the form of a numerical score or value relating to the likelihood that the patient has an elevated LVEDP using the plurality of values associated with the plurality of features assessing synchronicity between the cardiac signal and the photoplethysmographic signal and features associated with respective cardiac signal and the photoplethysmographic signal. The estimated value (e.g., as an elevated LVEDP score) for the likelihood the patient has an elevated LVEDP may be outputted for use in a diagnosis and/or treatment of a disease or condition such as, e.g., one or more forms of heart failure.

FIG. 3B shows an example of feature module(s) 122 (shown as 122a) which can be used in the LVEDP assessment operation and workflow. Modules 122 provide a pool of features that can be assessed to provide the best estimate for the assessment of elevated LVEDP. The number of features and feature classes may be adjusted while still being able to provide an estimation.

Depolarization/Repolarization Waveform Propagation features (Module(s) 340). This first class of features quantifies the propagative characteristics of the ventricular depolarization (VD) wave or ventricular repolarization (VR) wave by putting the acquired signal waveforms in three-dimensional space. The main wave characteristics are then categorized into four groups in this data space based on the 1. velocity, 2. trajectory, 3. orbital frequency (3D rotation rate), and 4. planarity of the wave signals. Examples of these analyses may be found in [1].

An example feature (e.g., QRS_max_Curvature_sub5) calculates the maximum curvature for a VD wave (also referred to as QRS signals in ECG lexicons) at the 5th frequency sub-band. Another example feature (e.g., T_max_OrbitalFrequency_sub14) calculates the maximum orbital frequency for the VR wave at the 14th frequency sub-band.

In addition to VD wave and VR wave, the wave propagation features are also applied to filtered VD waves and filtered VR waves at various frequency sub-bands. Tables 1A and 1B provide a list of depolarization waveform propagation features and repolarization waveform propagation features, respectively, that are used in the assessment of elevated LVEDP that can be implemented in Module(s) 340.

TABLE 1A

| Feature Name | Feature Name |
| --- | --- |
| QRS_median_Plan/srity_sub2 | QRS_minMaxRatio_Curvature_sub15; |
| QRS_min_Plan/srity_sub2 | QRS_max_OrbitalFrequency_sub5; |
| QRS_max_Plan/srity_sub2 | QRS_min_Plan/srity_sub14; |
| QRS_minMaxRatio_OrbitalFrequency_sub10 | QRS_min_Plan/srity_sub13; |
| QRS_median_Curvature_sub7 | QRS_minMaxRatio_NormalizedSpeed_sub15; |
| QRS_minMaxRatio_Plan/srity_sub1 | QRS_min_NormalizedSpeed_sub14; |

TABLE 1A-continued

| Feature Name | Feature Name |
| --- | --- |
| QRS_min_NormalizedSpeed_sub13 | QRS_max_NormalizedSpeed_sub12; |
| QRS_min_OrbitalFrequency_sub8 | QRS_max_OrbitalFrequency_sub1; |
| QRS_max_Plan/srity_sub15 | QRS_min_NormalizedSpeed_sub15 |
| QRS_minMaxRatio_Plan/srity_sub12 | QRS_median_Plan/srity_sub14 |
| QRS_minMaxRatio_NormalizedSpeed_sub1 | |

TABLE 1B

| Feature Name | Feature Name |
| --- | --- |
| T_minMaxRatio_Plan/srity_sub2 | T_max_NormalizedSpeed_sub7 |
| T_min_Plan/srity_sub11 | T_minMaxRatio_NormalizedSpeed_sub13 |
| T_max_Plan/srity_sub11 | T_median_NormalizedSpeed_sub13 |
| T_max_Plan/srity_sub4 | T_max_NormalizedSpeed_sub13 |
| T_median_Plan/srity_sub8 | T_max_Plan/srity_sub6 |
| T_minMaxRatio_Plan/srity_sub4 | T_minMaxRatio_NormalizedSpeed_sub14 |
| T_minMaxRatio_NormalizedSpeed_sub4 | T_min_NormalizedSpeed_sub8 |
| T_max_Plan/srity_sub12 | T_min_Curvature_sub7 |
| T_min_Plan/srity_sub7 | T_min_OrbitalFrequency_sub9 |
| T_max_Curvature_sub13 | T_min_Curvature_sub13 |
| T_min_NormalizedSpeed_sub14 | T_minMaxRatio_NormalizedSpeed_sub11 |
| T_max_NormalizedSpeed_sub15 | T_median_OrbitalFrequency_sub4 |
| T_median_Plan/srity_sub2 | T_median_NormalizedSpeed_sub4 |
| T_min_Curvature_sub15 | T_median_NormalizedSpeed_sub8 |
| T_min_NormalizedSpeed_sub2 | T_min_NormalizedSpeed_sub6 |
| T_minMaxRatio_Curvature_sub3 | T_minMaxRatio_Curvature_sub13 |
| T_min_NormalizedSpeed_sub7 | T_min_NormalizedSpeed_sub12 |
| T_min_NormalizedSpeed_sub5 | T_minMaxRatio_Curvature_sub8 |
| T_max_NormalizedSpeed_sub3 | T_minMaxRatio_NormalizedSpeed_sub6 |
| T_minMaxRatio_OrbitalFrequency_sub9 | T_max_Curvature_sub6 |
| T_median_Curvature_sub4 | T_max_Plan/srity_sub14 |
| T_median_Plan/srity_sub16 | T_max_NormalizedSpeed_sub8 |
| T_minMaxRatio_OrbitalFrequency_sub16 | T_max_NormalizedSpeed_sub2 |
| T_max_NormalizedSpeed_sub12 | T_median_Curvature_sub16 |
| T_min_NormalizedSpeed_sub13 | T_min_Plan/srity_sub8 |
| T_median_Plan/srity_sub15 | T_max_OrbitalFrequency_sub9 |
| T_max_OrbitalFrequency_sub4 | T_minMaxRatio_NormalizedSpeed_sub7 |
| T_minMaxRatio_OrbitalFrequency_sub8 | T_max_NormalizedSpeed_sub4 |

Depolarization Wave Propagation Deviation features (Module(s) 330). This second class of features can quantify deviations of the VD wave trajectory and the trajectory of a three-dimensional model of the same. By representing the model in a lower-dimensional space that also embeds the most prominent frequency content of the original signal below 40 Hz, these features can evaluate the high-frequency and low-amplitude patterns in the VD wave trajectory.

An example feature (e.g., maxCondDist) can calculate the maximum three-dimensional Euclidian distance between the model and the original VD wave.

Table 1C provides a list of depolarization waveform propagation deviation features that are used in the assessment of elevated LVEDP that can be implemented in Module(s) 330. Additional description of these features may be found in U.S. Provisional Patent Application No. 63/235, 974, filed Aug. 23, 2021, entitled "Methods and Systems for Engineering Conduction Deviation Features From Biophysical Signals for Use in Characterizing Physiological Systems," which is incorporated by reference herein in its entirety.

TABLE 1C

| Feature Name | Feature Name |
| --- | --- |
| relCondDelay_Z | MaxCondDelay_YZLag_PoincarePerimSurface AreaRatio |
| MaxCondDelay_XZLag_PoincareAlpha | MaxCondDelay_YZPerimSurfaceAreaRatio |

Cycle Variability features (Module(s) 336). This third class of features can quantify the beat-to-beat variations in biopotential by comparing each beat to a template beat. The template beat is the most prominent waveform represented across the entire signal acquired by applying the median filter to the stacked beat-to-beat segmented signal through VD peak matching.

An example feature (e.g., CVscore_X) calculates the distance between the signal and the template beat at the baseline (the section of the signal with no electrical activity) at channel X of a cardiac signal as a score value.

Table 1D provides a list of the depolarization cycle-variability features that are used in the assessment of elevated LVEDP that can be implemented in Module(s) 336. Additional description of these features may be found in U.S. Provisional Patent Application No. 63/130,324, entitled "Method and System to Assess Disease Using Cycle Variability Analysis of Biophysical Signals," which is incorporated by reference herein in its entirety.

TABLE 1D

| Feature Name | Feature Name |
| --- | --- |
| CV_Z_std | CV_PerimeterXY |
| CV_PerimeterYZ | CV_X_Skew |
| CV_VoidVolume | CV_Volume |
| CV_SurfaceArea | CV_X_std |
| CV_score_X. | |

Dynamical Systems (DS) features (Module(s) 334). This fourth class of features can quantify the dynamical characteristics of the biophysical signals, such as cardiac/biopotential channels and PPG signals. Examples of the dynamical characteristics include Lyapunov exponent, correlation dimension, entropy, mutual information, correlation, and nonlinear filtering.

An example feature (e.g., LEX) calculates the Lyapunov exponent of a biopotential channel X.

Table 1E provides a list of dynamical system features that are used in the assessment of elevated LVEDP that can be implemented in Module(s) 334. Additional description of these features may be found in U.S. patent application Ser. No. 16/831,264, entitled "Method and System to Assess Disease Using Dynamical Analysis of Biophysical Signals," which is incorporated by reference herein in its entirety.

TABLE 1E

| Feature Name | Feature Name |
| --- | --- |
| LEZ | SpXCFLUMax |
| CsLEX | SpCsXCFUXZ1 |
| SpXMILUR | SpD2L |
| SpXCFLU1 | SpCsXCFLXDelay |

Linear features (Module(s) 342). This fifth class of features can quantify both the morphological aspects within the waveforms of a biophysical measurement and variations therein, e.g., in cardiac/bipotential signals or PPG signals. For PPG signals, morphological aspects of waveforms in VPG and APG signals determined from a PPG signal may be assessed. Examples of these morphologic linear features can include waveform amplitudes, durations, geometric topology, among other morphologies.

An example feature (e.g., orth1_std_repolarizationDuration) calculates the repolarization duration for each beat in channel X. Multiple cycles may be evaluated in this manner, and the standard deviation of the analysis among the cycles can be determined. Another example feature (lowVPG_mean_peakDist) calculates the peak-to-peak distance between the prominent peaks of a VPG for each beat among the many beats performed by the analysis. The mean distance is then determined to quantify the results across the cycles.

Tables 1F and 1G provide a list of linear features in cardiac/biopotential signals and PPG signals, respectively, that are used in the assessment of elevated LVEDP that can be implemented in Module(s) 342. Additional description of these features may be found in U.S. Provisional Patent Application No. 63/235,971, filed Aug. 23, 2021, entitled "Methods and Systems for Engineering photoplethysmographic Waveform Features for Use in Characterizing Physiological Systems," which is incorporated by reference herein in its entirety.

TABLE 1F

| Feature Name | Feature Name |
| --- | --- |
| orth3_std_atrialDepolarizationPeakAmplitude | orth1_median_intraventricularSeptumDepolarizationDuration |
| orth1_normalizedDepolarizationRepolarizationInterval | orth3_normalizedDepolarizationRepolarizationInterval |
| orth1_median_atrialDepolarizationVentricularDepolarizationPeakDelay | orth3_std_repolarizationPotential |
| orth3_std_atrialDepolarizationVentricularDepolarizationPeakDelay | orth3_std_depolarizationInterval |
| orth2_std_atrialDepolarizationVentricularDepolarizationPeakDelay | orth3_median_depolarizationRepolarizationInterval |
| orth1_median_atrialDepolarizationPeakAmplitude | orth2_std_depolarizationInterval |
| orth3_std_ventricularRepolarizationPeakAmplitude | orth3_std_ventricularRepolarizationDuration |
| orth1_numUniqueMorphologies | orth2_std_repolarizationPotential |
| orth3_std_depolarizationRepolarizationInterval | orth3_std_septalDepolarizationPeakAmplitude |
| orth1_median_septalDepolarizationPeakAmplitude | orth2_std_atrialDepolarizationPeakAmplitude |
| orth3_median_ventricularDepolarizationRepolarizationPeakDelay | orth1_std_ventricularRepolarizationPeakAmplitude |
| orth2_std_atrialDepolarizationDuration | orth2_std_ventricularRepolarizationPeakAmplitude |
| orth2_std_depolarizationDuration | orth2_median_ventricularRepolarizationDepolarizationDelay |

TABLE 1G

| Feature Name | Feature Name |
| --- | --- |
| lowVPG_mean_min | upPPG_Tri1_P3angle |
| lowPPG_max_systPeak | upPPG_Tri3_area |
| lowPPG_max_pulseBase | upVPG_min_min |
| upAPG_mean_base | lowVPG_min_peak |
| lowPPG_mean_systPeak | lowVPG_mean_peak |
| lowVPG_max_base | upPPG_mean_systPeak |
| lowPPG_min_systPeak | upPPG_Tri1_P1angle |
| upPPG_Tri2_P3angle | upPPG_Tri1_P2angle |
| lowVPG_max_min | upPPG_Tri3_P1angle |
| lowVPG_mean_base | upPPG_max_pulseBase |
| lowPPG_mean_pulseBase | upVPG_mean_base |
| lowPPG_std_systPeak | upPPG_min_systPeak |
| lowVPG_min_base | upVPG_max_min |
| upPPG_Tri2_area | upPPG_Tri2_P1angle |
| upPPG_max_systPeak | upAPG_mean_peak |
| upPPG_mean_pulseBase | lowAPG_max_peak |
| lowVPG_mean_minDist_left | upPPG_Tri1_area |
| upPPG_Tri2_P2angle | lowAPG_mean_minDist |
| upPPG_Tri3_P3angle | lowPPG_min_pulseBase |
| upVPG_max_peak | lowPPG_mean_pulseDist_left |
| upVPG_max_base | lowAPG_mean_base |
| upVPG_min_base | upVPG_minMax_base |
| upPPG_Tri3_P2angle | lowVPG_max_peak |
| lowVPG_min_min | lowVPG_minMax_base |

Power Spectral and Wavelet Features (Module(s) 338). This sixth class of features can quantify the power spectrum and frequency content of specific regions of the acquired waveform for a biophysical signal such as a cardiac/biopotential signal and PPG signals. The analysis may be based on power spectrum analysis and coherence (cross-spectral analysis) analysis. Features can be determined from wavelet analyses of specific regions of the biophysical signals (e.g., ventricular depolarization, ventricular repolarization, and atrial depolarization regions in cardiac/biopotential signals).

An example feature (e.g., cohKurt_PPG) calculates the kurtosis within a distribution of calculated coherence between a first and a second PPG spectrum. Another example feature (e.g., wtPwave_circularity_Y_median) calculates the circularity of a high-power spectral region in the atrial depolarization regions of a cardiac/biopotential signal. The analysis is performed over multiple cycles to provide a distribution of the results to which the mean of the distribution can be determined.

Tables 1H and 1I provide a list of power spectral features and wavelet features, respectively, that are used in the assessment of elevated LVEDP that can be implemented in Module(s) 338. Additional description of these features may be found in U.S. Provisional Patent Application No. 63/235, 963, filed Aug. 23, 2021, entitled "Methods and Systems for Engineering Power Spectral Features From Biophysical Signals for Use in Characterizing Physiological Systems" and U.S. Provisional Patent Application No. 63/235,968, filed Aug. 23, 2021, entitled "Methods and Systems for Engineering Wavelet-Based Features From Biophysical Signals for Use in Characterizing Physiological Systems," each of which is incorporated by reference herein in its entirety.

TABLE 1H

| Feature Name | Feature Name |
|---|---|
| cohKurt_PPG | DRM1_Red |
| pRatioM1M2_IR | TMFreq |
| pRatioM1M2_Red | coherence_entropy_XZ |
| LDM2_Red | ssr_XZ |
| pM1_Red | csr_sign/sl |
| LDM2_IR | coherence_std_XZ |
| pM1_IR | coherence_kurt_YZ |
| cohEntropy_PPG | coherence_skew_YZ |
| cohSkew_PPG | coherence_skew_XZ |
| cohSum_PPG | coherence_kurt_XZ |
| LDM1_Red | |

TABLE 1I

| Feature Name | Feature Name |
|---|---|
| wtQRSwaveDist_qqr2_Uniform_Y_n/snmedian | wtPwave_surface_Area_X_iqr |
| wtQRSwave_timeRange_Z_iqr | wtTwave_extent_X_median |
| wtTwave_timeRange_X_iqr | wtTwave_orientation_Y_iqr |
| wtTwaveDecay_powerCentroid_Decay_X_median | wtQRSwave_eccentricity_X_iqr |
| wtQRSwaveDist_pdfKernel_L1norm_X_n/snmedian | wtCohXY_eccentricity |
| wtQRSwaveDecay_timeCentroid_Decay_Z_median | wtPwave_eccentricity_Y_median |
| wtPwave_frequencyCentroid_X_iqr | wtTwave_circularity_X_iqr |
| wtTwaveDecay_timeRange_Decay_Y_median | wtQRSwave_frequencyRange_Z_iqr |
| wtTwaveDecay_eccentricity_Decay_Y_median | wtQRSwave_timeRange_X_iqr |
| wtTwaveDecay_timeCentroid_Decay_Z_median | wtPwave_circularity_Y_median |
| wtTwaveDecay_timeCentroid_Decay_Y_median | wtQRSwave_eccentricity_X_median |
| wtQRSwave_timeRange_X_median | wtTwave_timeCentroid_X_median |
| wtTwave_eccentricity_X_iqr | wtTwave_timeCentroid_Z_median |
| wtQRSwave_frequencyCentroid_Z_iqr | wtPwave_surfaceArea_X_median |
| wtQRSwave_orientation_Z_median | wtPwave_eccentricity_X_median |
| wtTwave_powerCentroid_Z_iqr | wtQRSwave_circularity_Z_iqr |
| wtQRSwaveDist_entropy_X_n/snmedian | wtTwaveDecay_extent_Decay_X_median |
| wtQRSwaveDecay_orientation_Decay_Z_median | wtQRSwave_frequencyRange_X_median |
| wtPwave_timeRange_X_iqr | wtQRSwave_frequencyCentroid_X_median |
| wtTwaveDecay_timeCentroid_Decay_X_median | wtQRSwave_extent_Z_median |
| wtPwaveDecay_numRegion/s_Decay_X_median | wtPwave_timeRange_Y_iqr |
| wtQRSwaveDist_qqr2_Normal_Y_n/snmedian | wtPwave_circularity_Y_iqr |
| wtPwaveDecay_eccentricity_Decay_X_median | wtPwaveDist_skewPSD_X_n/snmedian |
| wtQRSwaveDecay__frequencyCentroid_Decay_X_median | wtPwave_circularity_X_iqr |
| wtTwaveDecay_numRegion/sR2_Decay_X_median | wtTwave_frequencyRange_X_iqr |
| wtQRSwaveDist_cdfNormal_std_Y_n/snmedian | wtTwave_frequencyRange_Y_median |
| wtQRSwaveDist_qqslop_Uniform_X_n/snmedian | wtPwaveDist_skewPSD_Z_n/snmedian |
| wtQRSwaveDist_peakWidthPSD_X_n/snmedian | wtPwave_surfaceArea_Y_iqr |
| wtQRSwaveDist_qqsse_Uniform_Y_n/snmedian | wtQRSwave_timeCentroid_Y_iqr |
| wtQRSwaveDecay_circularity_Decay_Y_median | wtTwave_orientation_X_iqr |
| wtPwaveDist_qqsse_Uniform_Y_n/snmedian | wtTwave_timeRange_Z_median |
| wtQRSwaveDist_qqsse_Normal_X_n/snmedian | wtPwave_timeCentroid_Y_median |
| wtQRSwaveDist_pdftKernel_std_X_n/snmedian | wtPwave_circularity_X_median |
| wtTwaveDecay_timeRange_Decay_Z_median | wtTwave_timeRange_Y_median |
| wtQRSwave_eccentricity_Y_median | wtTwave_eccentricity_Z_median |
| wtQRSwaveDecay_orientation_Decay_X_median | wtPwave_timeCentroid_X_iqr |
| wtTwaveDist_peakWidthPSD_Y_n/snmedian | wtQRSwaveDecay_extent_Decay_Y_median |
| wtPwaveDist_peakDispPSD_Y_n/snmedian | wtQRSwave_timeCentroid_X_median |
| wtTwaveDist_pdftKernel_std_X_n/snmedian | wtTwave_circularity_Y_median |
| wtPwaveDecay_numRegion/sR2_Decay_Y_median | wtTwave_circularity_Z_median |
| wtQRSwaveDist_peakDispPSD_X_n/snmedian | wtPwave_timeCentroid_Y_iqr |
| wtPwaveDecay_frequency_Range_Decay_Z_median | wtTwave_frequencyCentroid_X_iqr |
| wtPwaveDist_medianPSD_Z_n/snmedian | wtPwave_timeRange_Y_median |
| wtTwaveDecay_circularity_Decay_Y_median | wtPwave_timeRange_Z_median |
| wtQRSwaveDist_qqslop_Normal_X_n/snmedian | wtQRSwave_frequencyCentroid_X_iqr |
| wtPwaveDist_peakWidthPSD_Y_n/snmedian | wtPwave_powerCentroid_Z_median |
| wtQRSwaveDecay_eccentricity_Decay_X_median | wtQRSwave_orientation_X_iqr |
| wtTwaveDecay_eccentricity_Decay_X_median | wtQRSwave_circularity_X_iqr |
| wtPwaveDecay_orientation_Decay_X_median | wtPwave_powerCentroid_Z_iqr |
| wtTwaveDecay_eccentricity_Decay_Z_median | wtQRSwave_timeCentroid_X_iqr |
| wtQRSwaveDist_cdfNormal_L1norm_Y_n/snmedian | wtTwave_timeCentroid_Y_median |

TABLE 1I-continued

| Feature Name | Feature Name |
|---|---|
| wtQRSwaveDist__stdPSD__X__n/snmedian | wtTwave__eccentricity__Y__median |
| wtTwaveDecay__circularity__Decay__X__median | wtTwave__extent__X__iqr |
| wtPwaveDecay__timeRange__Decay__Y__median | wtPwave__eccentricity__Y__iqr |
| wtQRSwaveDecay__timeCentroid__decay__X__median | wtCohXY__frequencyCentroid |
| wtTwaveDecay__circularity__Decay__Z__median | wtPwave__timeCentroid__Z__median |
| wtPwaveDist__cdfNormal__std__Z__n/snmedian | wtQRSwave__extent__Z__iqr |
| wtPwaveDecay__orientation__Decay__Z__median | wtPwave__timeCentroid__X__median |

Visual loop features (Module(s) 326). This seventh class of features can calculate the topologic aspects of distinct loop regions (e.g., atrial depolarization, ventricular depolarization, and ventricular repolarization) associated with the biophysical signals in three-dimensional phase space or 2D projections of them.

An example feature (e.g., lowerPPG_Circulation_PPGVPG) calculates the rotation of a first PPG loop 2D space plane defined by a PPG signal and a VPG phase.

Tables 1J and 1K provide a list of visual loop features in cardiac/biopotential signals and PPG signals, respectively, that are used in the assessment of elevated LVEDP that can be implemented in Module(s) 326. Additional description of these features may be found in U.S. Provisional Patent Application No. 63/236,072, filed Aug. 23, 2021, entitled "Methods and Systems for Engineering Visual Features From Biophysical Signals for Use in Characterizing Physiological Systems," which is incorporated by reference herein in its entirety.

TABLE 1J

| Feature Name | Feature Name |
|---|---|
| AD__2dArea__ORTH12__Overall | VR__Max2dAreaQuadNum__ORTH13 |
| AD__AverageVorticity | VR__Max2dPerimeterQuadNum__ORTH__13 |
| AD__Max2dAreaQuadNum__ORTH13 | VR__SurfaceArea__AlphaShape__Octant2 |
| AD__SurfaceArea__AlphaShape__Octant6 | VD__SurfaceArea__ConvexHull__Octant3 |
| AD__SurfaceArea__ConvexHull__Octant6 | VR__SurfaceArea__AlphaShape__Octant7 |
| AD__Volume__AlphaShape__Octant6 | VR__SurfaceArea__ConvexHull__Octant3 |
| AD__Volume__AlphaShape__Overall | VR__SurfaceArea__ConvexHull__Octant5 |
| AD__Volume__ConvexHull__Octant6 | VR__SurfaceArea__ConvexHull__Octant7 |
| IVDV__MVRV__3dAngle | VR__Volume__AlphaShape__Octant2 |
| MADV__2DAngle__ORTH13 | VR__Volume__AlphaShape__Octant5 |
| MADV__OctantNum | VR__Volume__AlphaShape__Octant7 |
| TVDV__2D__Amplitude__ORTH13 | VR__Volume__AlphaShape__Overall |
| VD__2dArea__ORTH12__Quad2 | VR__Volume__ConvexHull__Octant3 |
| VD__SurfaceArea__AlphaShape__Overall | VR__Volume__ConvexHull__Octant5 |
| VD__SurfaceArea__ConvexHull__Octant3 | VR__Volume__ConvexHull__Octant7 |
| VD__Volume__AlphaShape__Octant3 | VR__2dArea__ORTH12__Quad1 |
| VD__Volume__AlphaShape__Overall | VR__2dArea__ORTH13__Quad4 |
| VR__2dArea__ORTH12__Overall | VR__2dPerimeter__ORTH23__Quad3 |

TABLE 1K

| Feature Name | Feature Name |
|---|---|
| lowerPPG__diasPPG__2DAngle__VPGAPG | lowerPPG__peakAPG__2DAngle__PPGAPG |
| upperPPG__min/sPG__Elevation | upperPPG__peakAPG__2DAngle__PPGAPG |
| lowerPPG__diasPPG__2DAngle__PPGVPG | lowerPPG__AverageVelocity |
| upperPPG__diasPPG__2DAngle__VPGAPG | upperPPG__min/sPG__2DAmplitude__PPGAPG |
| upperPPG__baseAPG__Elevation | upperPPG__baseAPG__2DAmplitude__PPGVPG |
| lowerPPG__peakAPG__Elevation | lowerPPG__baseVPG__2DAngle__VPGAPG |
| upperPPG__3dPerimeter__Overall | lowerPPG__AverageVorticity |
| lowerPPG__2dPerimeter__PPGVPG__Overall | AD__Volume__AlphaShape__Octant6 |
| upperPPG__peakAPG__Elevation | VR__SurfaceArea__AlphaShape__Octant2 |
| upperPPG__2dPerimeter__PPGVPG__Overall | AD__AverageVorticity |
| upperPPG__min/sPG__2DAngle__VPGAPG | VR__SurfaceArea__AlphaShape__Octant5 |
| upperPPG__3dMeanCurvature | VR__Volume__ConvexHull__Octant5 |
| upperPPG__diasPPG__2DAngle__PPGVPG | VD__Volume__AlphaShape__Octant3 |
| upperPPG__AverageVelocity | VR__Max2dAreaQuadNum__ORTH1__3 |
| lowerPPG__baseAPG__Elevation | VR__SurfaceArea__ConvexHull__Octant5 |
| upperPPG__minVPG__2DAngle__VPGAPG | IVDV__MVRV__3dAngle |
| lowerPPG__Circulation__PPGVPG | AD__SurfaceArea__AlphaShape__Octant6 |
| upperPPG__Circulation | TVDV__2DAmplitude__ORTH13 |
| upperPPG__3dMaxCurvature | VR__Max2dPerimeterQuadNum__ORTH13 |
| lowerPPG__3dMeanCurvature | VR__Volume__ConvexHull__Octant7 |
| lowerPPG__sysPPG__2DAngle__PPGVPG | AD__SurfaceArea__ConvexHull__Octant6 |
| upperPPG__sysPPG__2DAngle__PPGVPG | VR__SurfaceArea__ConvexHull__Octant7 |
| lowerPPG__peakAPG__2DAmplitude__PPGAPG | AD__Volume__AlphaShape__Overall |
| lowerPPG__peakAPG__2DAngle__VPGAPG | VR__Volume__AlphaShape__Octant2 |
| upperPPG__minVPG__2DAngle__PPGAPG | VD__2dArea__ORTH12__Quad2 |

TABLE 1K-continued

| Feature Name | Feature Name |
| --- | --- |
| lowerPPG_3dMaxCurvature | VR_2dArea_ORTH13_Quad4 |
| lowerPPG_2dArea_PPGVPG_Overall | VR_SurfaceArea_AlphaShape_Octant7 |
| upperPPG_minVPG_Elevation | VR_SurfaceArea_ConvexHull_Octant3 |
| upperPPG_AverageVorticity | VR_Volume_ConvexHull_Octant3 |
| lowerPPG_diasPPG_Elevation | VD_SurfaceArea_AlphaShape_Overall |
| lowerPPG_3dPerimeter_Overall | VR_Volume_AlphaShape_Octant7 |
| lowerPPG_min/sPG_Elevation | VR_Volume_AlphaShape_Overall |
| lowerPPG_baseAPG_2DAmplitude_PPGVPG | AD_2dArea_ORTH12_Overall |
| lowerPPG_baseAPG_2DAngle_PPGAPG | AD_Volume_ConvexHull_Octant6 |
| lowerPPG_sysPPG_2DAngle_VPGAPG | VD_Volume_AlphaShape_Overall |
| upperPPG_baseVPG_2DAngle_VPGAPG | VR_Volume_AlphaShape_Octant5 |
| upperPPG_baseAPG_3D_Amplitude | AD_Max2dAreaQuadNum_ORTH13 |
| lowerPPG_diasPPG_2DAmplitude_VPGAPG | VR_2dPerimeter_ORTH23_Quad3 |
| lowerPPGCirculation | MADV_2DAngle_ORTH13 |
| upperPPG_baseAPG_2DAmplitude_PPGAPG | VR_2dArea_ORTH12_Quad1 |
| lowerPPGbaseAPG_3DAmplitude | VR_2dArea_ORTH12_Overall |
| lowerPPG_peakAPG_3DAmplitude | MADV_OctantNum |

Predictability features (Module(s) 324). This eight class of features can quantify the predictability of the biophysical signal as measured by the ability of a model trained on a majority (e.g., 75%) of the signal to predict the remaining (e.g., 25%). Features are formed from predictability error and statistics of residues condensed from nonlinear filtering techniques.

An example feature (e.g., StdResX) calculates the standard deviation of residue from a nonlinear filtering technique performs on a cardiac signal channel X.

Table 1L provides a list of predictability features that are used in the assessment of elevated LVEDP that can be implemented in Module(s) 324.

TABLE 1L

| Feature Name | Feature Name |
| --- | --- |
| StdResZ | PcntResX |
| InfoDimX | PcntResZ |
| InfoDimY | KurtResZ |
| InfoDimZ | StdResY |
| PcntResY | |

Respiration features (Module(s) 328). This ninth class of features can approximate the respiration waveform and evaluate the characteristics of that approximation. Modulation signals are produced on each input signal and fused. Features are determined based on heart rate variability, respiration rate information, discrepancies representing the distance between respiration and modulation signals, square coherence representing the correlation between modulation and respiration rate signals.

An example feature (e.g., dFmPPGMMDStd) uses the frequency modulation signal from a PPG signal and calculates the maximum mean discrepancy of each cycle among a plurality of cycles. The mean of the distribution from those analyses is outputted as the feature.

Table 1M provides a list of respiration features that are used in the assessment of elevated LVEDP that can be implemented in Module(s) 328. Additional description of these features may be found in U.S. Provisional Patent Application No. 63/235,966, filed Aug. 23, 2021, entitled "Method and System for Engineering Rate-Related Features_From Biophysical Signals for Use in Characterizing Physiological Systems," which is incorporated by reference herein in its entirety.

TABLE 1M

| Feature Name | Feature Name |
| --- | --- |
| dAmECGEntMean | dRRMean |
| dFmECGEntMean | dAmECGMMDKurt |
| dHRVSkewPPG | dAmECGCXYStd |
| dAmPPGMMDKurt | dPkPPGEntMean |
| dAmPPGEntMean | dAmPPGEntStd |
| dFmPPGCXYMean | dPkPPGCXYMean |
| dAmECGMMDSkew | dPkECGEntMean |
| dHRVStdPPG | dPkPPGEntStd |
| dFmPPGEntSkew | dAmPPGMMDMean |

Poincaré and Synchronicity features (Module(s) 322). This tenth class of features calculates the time difference between the peaks identified within the waveforms of a biophysical signal and uses that calculated time difference as input to a Poincaré analysis to quantify the signal dynamics. Within the Poincaré analysis, the features can be extracted that characterize the synchronicity characteristics between the different modalities of the biophysical signals, e.g., between cardiac/biopotential signals and PPG signals.

An example feature (e.g., numberOfKernelDensity-Modes) calculates the number of distinct peaks in the kernel density estimate of the PPG peak time differences.

Table 1N provides a list of Poincaré and synchronicity features that are used in the assessment of elevated LVEDP that can be implemented in Module(s) 322. Additional description of these features may be found in U.S. patent application Ser. No. 16/831,380, entitled "Method and System to Assess Disease Using Dynamical Analysis of Cardiac and Photoplethysmographic Signals," which is incorporated by reference herein in its entirety.

TABLE 1N

| Feature Name | Feature Name |
| --- | --- |
| dZDmn | dModeLP |
| dModeUP | dYMode2 |
| dMeanU | dDmnL |
| dAlphaLUXR | dStdLURP1 |
| dMeanL | dPhiDiffXLMean |
| dKurtL | dPhiDiffXL1Med |
| dDmnU | dPhiDiffXL2Med |
| dRelStdMADL | largestClusterEllipse.X0 |

Physiological features (Module(s) 332). This eleventh class of features can quantify specific physiological aspects of a biopotential signal.

An example feature (e.g., morphology_X) quantifies the categorical morphology of the atrial depolarization.

Table 1P provides a list of Physiological features that are used in the assessment of elevated LVEDP that can be implemented in Module(s) 332. Additional descriptions of these features may be found in U.S. patent provisional application No. 63,236,193, filed Aug. 23, 2021, entitled "Method and System for Engineering Cardiac Waveform Features from Biophysical Signals for Use in Characterizing Physiological Systems," which is incorporated by reference herein in its entirety.

TABLE 1P

| Feature Name | Feature Name |
| --- | --- |
| dist_termin/slSegment_I | area_secondWave_V1 |
| waveDuration_II | morphology_X |
| areaRatio_X | |

Example Visualization Output of a Clinical
Evaluation System

Figure 4:
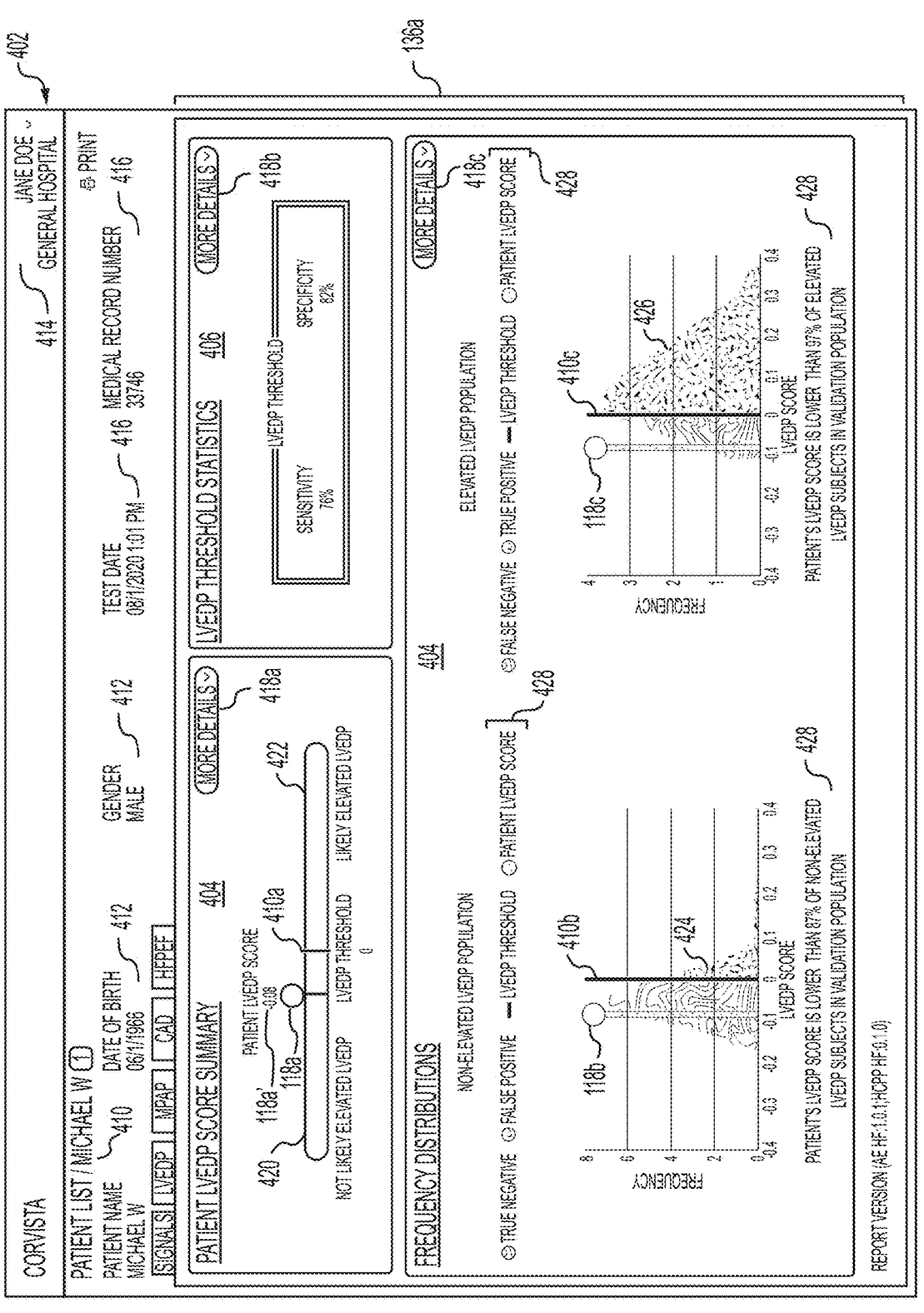
FIG. 4 shows an example visualization output of the clinical evaluation system of FIG. 1.

Clinical evaluation system 103a can generate in certain implementations an estimate of the presence or non-presence of elevated LVEDP (e.g., the likelihood that the patient has an elevated LVEDP). FIG. 4 shows an example patient report 402 that includes a visualization 136 (shown as 136a) of an output score 118 (shown as 118a, 118b, and 118c) generated by the classifier model (e.g., 134) of a clinical evaluation system 103 (shown as 103a).

Clinical evaluation system 103a may include or can operate with a healthcare provider portal 813 (not shown—see FIG. 8) configured to present the patient's report 402 in a user interface. In some embodiments, the healthcare provider portal (e.g., 813) employs a web-service application to provide the patient's report 402 to a remote terminal that is accessible by a healthcare provider, a lab technician, the patient, or the patient's family. In other embodiments, report 402 is transmitted to the biophysical signal capture system (e.g., 102), a patient-owned device, or other display system described herein. To this end, the user interface can be a graphical user interface that can be executed on a desktop computer, tablet, mobile device (e.g., smartphone, smart-watch), measurement device, etc.

Report 402 may present the output score (e.g., 118) in multiple views in the user interface. In the example shown in FIG. 4, the report 402 includes a score summary section 404 (shown as "Patient LVEDP Score Summary" section 404), a threshold section 406 (shown as "LVEDP Threshold Statistics" section 406), and a frequency distribution section 408 (shown as "Frequency Distribution" section 408). Report 402 also presents other patient information 412 (e.g., identifier, date of birth or age, gender), service provider information 414 (e.g., acquisition location, technician or physician performing the acquisition), and acquisition information 416 (e.g., test date, medical record number). In each of the sections (e.g., 402, 404, 406), Report 402 may include buttons or inputs 418 (shown as 418a, 418b, 418c) that provide panel-specific information and explanation.

Report 402 may indicate a disease-specific result (e.g., elevated LVEDP) being available if the signal analysis could be performed. The patient's estimated score (shown via visual element 602a) may be interpreted relative to an established threshold 410 (shown as 410a, 410b, 410c) in one more visualization. In the example of FIG. 4, the score

118 is an estimation that provides a likelihood of the presence of a disease, condition, or an indication of either one (e.g., elevated LVEDP) and can be established relative to a validation population in the assessment of that disease, condition, or indication, e.g., using a binary search. If the patient score matches the validation population, that value is presented. If the patient score does not exist within the population, then the location of the closest available score would be used. For example, if the score is 0.55, and the validation population includes scores of 0.52, 0.54, 0.57, then the location of 0.54 may be presented and used to calculate the percentile.

In the score summary section 404 shown in the example of FIG. 4, the patient's score (118a) and associated threshold (410a) is superimposed on a two-tone color bar with the threshold located at the center of the bar with a defined value of "0" representing the delineation between test positive and test negative. The left of the threshold (bar section 420) may be shaded with a lighter color and indicates a negative test result (e.g., "Not Likely Elevated LVEDP"), while to the right of the threshold (bar section 422) may be shaded a darker color and indicates a positive test result (e.g., "Likely Elevated LVEDP"). The score 118a may include a visual graph indicator (shown as 118a) and a numerical indicator (shown as 118a'). The threshold value, in this implementation, is constant and does not change patient-to-patient.

The threshold section 406 shows reported statistics of the threshold as provided to a validation population that defines the sensitivity and specificity for the estimation. The threshold is the same for every test regardless of the individual patient's score 118, meaning that every score, positive or negative, may be interpreted for accuracy in view of the provided sensitivity and specificity information. The score may change for a given disease-specific analysis as well with the updating of the clinical evaluation.

The frequency distribution section 408 illustrates the distribution of all patients in two validation populations (e.g., (i) a non-elevated population to indicate the likelihood of a false positive estimation and (ii) an elevated population to indicate a likelihood of a false negative estimation). The graphs (424, 426) are presented as smooth histograms to provide context for interpreting the patient's score 118 (e.g., 118b, 118c) relative to the test performance validation population patients.

The frequency distribution section 408 includes a first graph 424 (shown as "Non-Elevated LVEDP Population" 424) that shows the score (118b), indicating the likelihood of the non-presence of the disease, condition, or indication, within a distribution of a validation population having non-presence of that disease, condition, or indication and a second graph 426 (shown as "Elevated LVEDP Population" 426) that shows the store (118c), indicates the likelihood of the presence of the disease, condition, or indication, within a distribution of validation population having the presence of that disease, condition, or indication.

In the example of the assessment of elevated LVDEP, the first graph 424 shows a non-elevated LVEDP distribution of the validation population that identifies the true negative (TN) and false positive (FP) areas. The score 118b is shown in graph 424 along with the threshold 410b. In this same example, the second graph 426 shows an elevated LVEDP distribution of the validation population that identifies the false negative (TN) and true positive (FP) areas. The score 118c is shown in graph 426 along with the threshold 410c.

The frequency distribution section 408 also includes interpretative text 428 of the patient's score relative to other patients in a validation population group (as a percentage).

In this example, the patient has an LVEDP score of –0.08, which is located to the left side of the LVEDP threshold, indicating that the patient has "Not Likely Elevated LVEDP."

The report may be presented in the healthcare portal, e.g., to be used by a physician or healthcare provider in their diagnosis for indications of left-heart failure. The indications include, in some embodiments, a probability or a severity score for the presence of elevated LVEDP. In other embodiment, the indications include a probability or a severity score for the presence of a condition that could lead to left-heart failure or a likelihood that left-heart failure can result within a certain time frame.

The clinical evaluation system may generate a report for a patient only if a given patient's acquired signal data set meets the signal quality standards as assessed by the signal quality assessment function described herein. The healthcare provider portal may indicate the patient signal acquisition failing to meet signal requirements for a report to be generated. In other embodiments, the healthcare provider portal may not provide an indication that a failed acquisition was made. In some embodiments, such a report may be provided even if the signal quality standards are not met.

Experimental Results and Examples

Several development studies have been conducted to develop feature sets, and in turn, algorithms that can be used to estimate the presence or non-presence, severity, or localization of disease, medical condition, or an indication of either. In one study, algorithms were developed for the non-invasive assessment of abnormal or elevated LVEDP, including those described herein. As noted above, abnormal or elevated LVEDP is an indicator of heart failure in its various forms. In another development study, algorithms and features were developed for the non-invasive assessment of coronary artery disease.

As part of these two development studies, clinical data were collected from adult human subjects using a biophysical signal capture system and according to protocols described in relation to FIG. 2. The subjects underwent cardiac catheterization (the current "gold standard" tests for CAD and abnormal LVEDP evaluation) following the signal acquisition, and the catheterization results were evaluated for CAD labels and elevated LVEDP values. The collected data were stratified into separate cohorts: one for feature/algorithm development and the other for their validation.

Within the feature development phases, features were developed, including several of features associated with modules 322, 324, 326, 328, 330, 332, 334, 336, 338, 340, 342, among other features, to extract characteristics in an analytical framework from biopotential signals (as an example of the cardiac signals discussed herein) and photo-absorption signals (as examples of the hemodynamic or photoplethysmographic discussed herein) that are intended to represent properties of the cardiovascular system. Corresponding classifiers were also developed using classifier models, linear models (e.g., Elastic Net), decision tree models (XGB Classifier, random forest models, etc.), support vector machine models, and neural network models to non-invasively estimate the presence of an elevated or abnormal LVEDP. Univariate feature selection assessments and cross-validation operations were performed to identify features for use in machine learning models (e.g., classifiers) for the specific disease indication of interest.

Figure 5:
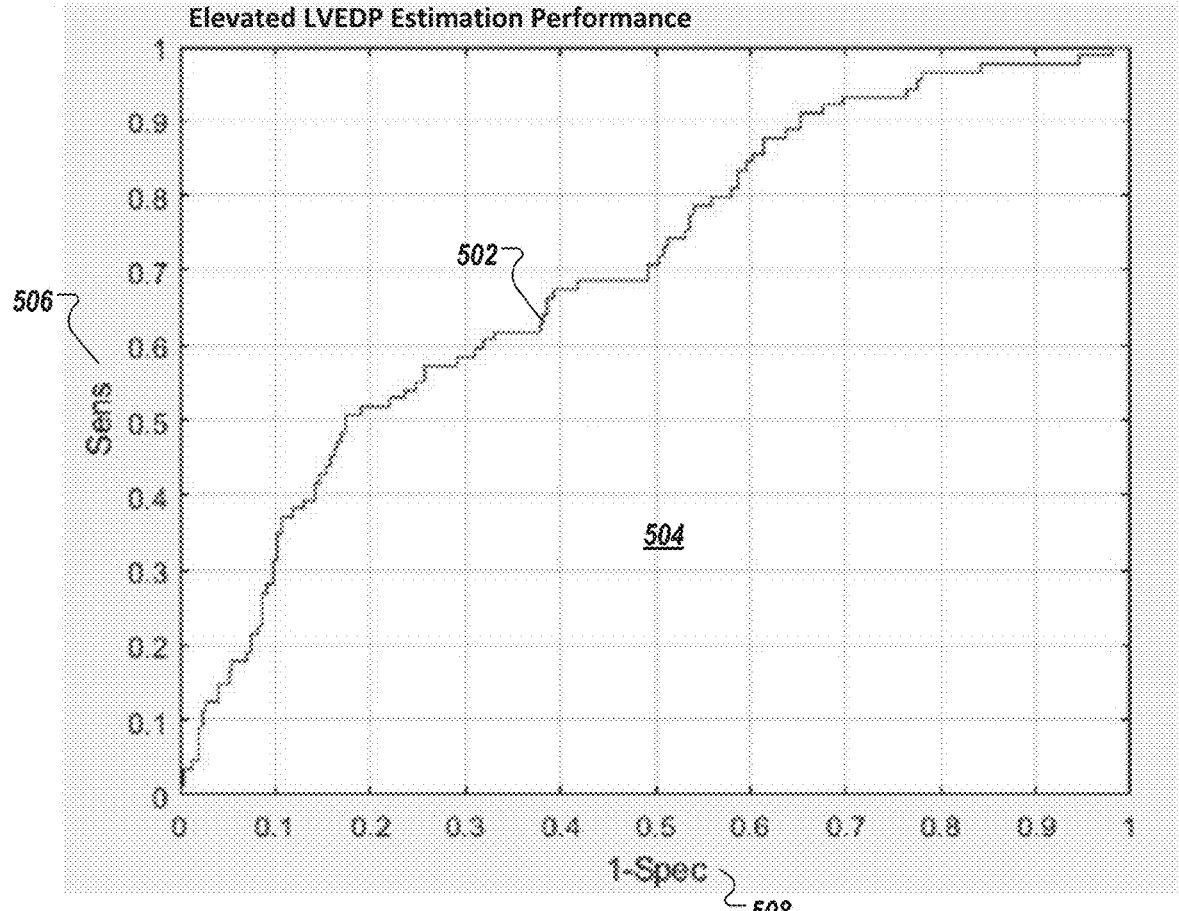
FIG. 5 shows the performance of the clinical evaluation system of FIG. 1 with a ROC curve.

FIG. 5 shows the performance of the classifier (e.g., 134) for the elevated LVEDP estimation/assessment algorithm that employs the features of modules 322, 324, 326, 328, 330, 332, 334, 336, 338, 340, 342 in a receiver operating characteristic (ROC) curve (502) of 1-specificity vs. sensitivity. The ROC curve (502) illustrates the diagnostic ability of a classifier system (e.g., 134) as its discrimination threshold is varied. The ROC curve may be created by plotting the true positive rate (TPR) against the false positive rate (FPR) at various threshold settings. AUC-ROC quantifies the area under a receiver operating characteristic (ROC) curve—the larger this area, the more diagnostically useful the model is at accurately performing the classification. The ROC, and AUC-ROC, value is considered statistically significant when the bottom end of the 95% confidence interval is greater than 0.50. In the example ROC curve 502 of FIG. 5, the y-axis (506) (shown as the sensitivity axis ("Sens" 506) can be defined as $$sens = \frac{TP}{TP+FN}$$

and the axis (508) (shown as "1-Spec" 508) can be defined as $$1-spec = \frac{FP}{TN+FP}$$

in which TP is the probability of a true positive, FN is the probability of a false negative, TN the probability of a true negative, and FP is the probability of a false positive.

In the example of FIG. 5, a threshold of 0.39 is selected to provide the optimal yield performance having a specificity of 82% and a sensitivity of 76% among a set of validation data in estimating the likelihood of a patient having elevated LVEDP. This specificity and sensitivity performance is comparable to the gold standard techniques for the assessment of elevated LVEDP (namely cardiac catheterization), which is a highly invasive assessment method. Notably, the exemplary system and method can provide a similar clinical assessment using non-invasively acquired measurements (e.g., cardiac and PPG signals) that can be acquired from surface-based sensors placed on the patient while at rest. Indeed, the ROC curve 502 (and corresponding AUC 504) shows the elevated LVEDP estimation/assessment algorithm disclosed herein having significant utility in the assessment of the presence or non-presence of elevated LVEDP.

The threshold can be selected to optimally establish the threshold that maximizes areas of the true positive (FP) and true negative (TN) while minimizing the areas of the false positive (FP), false negative (TN) within the validation populations. The selected threshold value (e.g., 0.39 discussed above) can be subtracted from all the predictions to center the threshold at zero; therefore, any prediction greater than or equal to zero is test-positive, and any prediction less than zero is test-negative.

Example Development System

Figure 6:
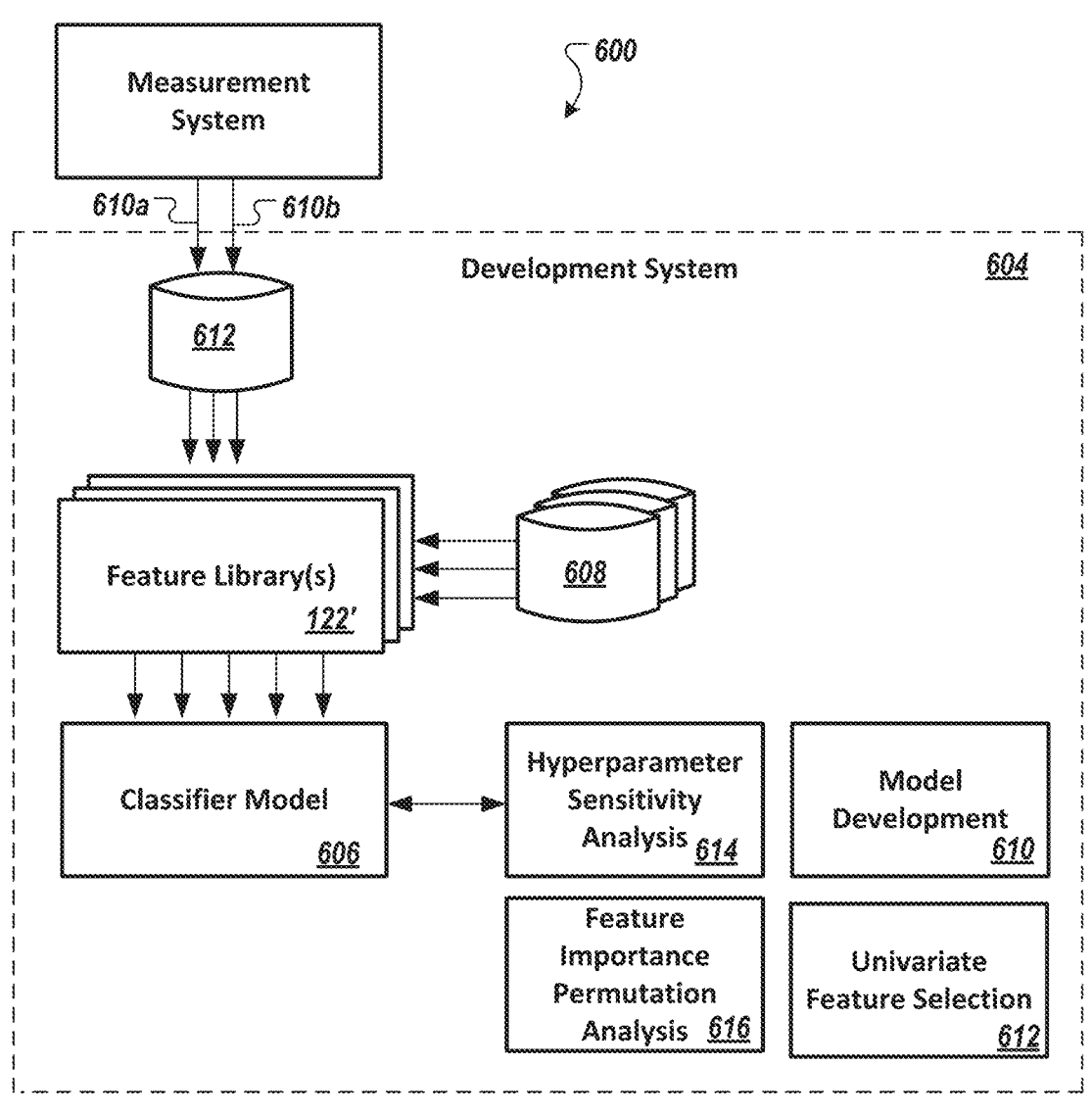
FIG. 6 is a diagram of a development system and environment that can be used to develop and assess a clinical evaluation system that can predict and/or estimate presence, non-presence, localization, and/or severity of a metric/estimate associated with a disease, condition, or indicator of one in a patient, including the clinical evaluation system of FIG. 1.

FIG. 6 is a diagram of a development system 600 that can be used to develop and evaluate a clinical assessment system (e.g., system 103) that can estimate (e.g., determine) the likelihood of the presence, non-presence, localization, and/or or severity of a metric/estimate (e.g., elevated LVEDP) associated with a disease or condition in such physiological system, including for elevated LVEDP as disclosed herein, in accordance with an illustrative embodiment. The development system 600 can be used to assess and develop analytical engines for various clinical applications discussed herein.

Development system 604 can include a set of feature library module(s) (e.g., 122' and 608), classifier model module(s) 606, training data set repository 612, model development module 610, univariate feature selection module 612, hyperparameter sensitivity analysis module 614, and feature importance permutation analysis 616. Development system 604 may employ one or more of these modules to select features prior to classifier or model development by isolating features that are stable, meaningful, and statistically linked to a patient's disease, medical condition, or indication of either. Features that do not pass through the selection step can be excluded from machine learning for the specific disease, condition, or indication.

Feature Library Module. The feature library module 122 (shown as 122') can include feature (e.g., from modules 322, 324, 326, 328, 330, 332, 334, 336, 338, 340, 342). Other feature modules may be employed by the development system 604, shown as features modules 608, e.g., including those that are described in U.S. Pat. Nos. 9,289,150; 9,655,536; 9,968,275; 8,923,958; 9,408,543; 9,955,883; 9,737,229; 10,039,468; 9,597,021; 9,968,265; 9,910,964; 10,672,518; 10,566,091; 10,566,092; 10,542,897; 10,362,950; 10,292,596; 10,806,349; U.S. Patent Publication nos. 2020/0335217; 2020/0229724; 2019/0214137; 2018/0249960; 2019/0200893; 2019/0384757; 2020/0211713; 2019/0365265; 2020/0205739; 2020/0205745; 2019/0026430; 2019/0026431; PCT Publication nos. WO2017/033164; WO2017/221221; WO2019/130272; WO2018/158749; WO2019/077414; WO2019/130273; WO2019/244043; WO2020/136569; WO2019/234587; WO2020/136570; WO2020/136571; U.S. patent application Ser. Nos. 16/831,264; 16/831,380; 17/132,869; PCT Application nos. PCT/1132020/052889; PCT/1132020/052890, each of which is hereby incorporated by reference herein in its entirety. While the run-time system, e.g., of FIG. 1 may include some or only features used for a given clinical evaluation (e.g., tens to hundreds of features), the feature libraries 608 of the development system 604 can include the full set of features (or a substantial portion) to be evaluated for a given clinical application (e.g., in the hundreds to thousands of features).

Classifier Model Module. The classifier model module 606 can include instructions for a plurality of configured machine learning and regression models, such as, but not limited to, decision trees, random forests, SVMs, neural networks, linear models, Gaussian processes, nearest neighbor, SVMs and Naïve Bayes, including those described in relation to FIG. 1. The classifier model module 606 can include instructions for commercially available machine learning and regression models (e.g., as manufactured by Caret or Mathworks) or custom machine learning and regression models, e.g., configured by the model development module 610 and other development modules described herein (e.g., 614, 614, 616). In some embodiments, the classifier model module(s) 606 is configured with a corresponding configuration operation to tune or configure the machine learning and regression models.

The classifier model module 606 may include machine learning and regression models for the assessment of elevated or abnormal left ventricular end-diastolic pressure (LVEDP) as well as various other clinical applications as discussed herein.

Data Set Repository. The training data set repository 612 includes acquired, labeled biophysical data sets (e.g., for cardiac, photoplethysmographic, ballistocardiographic, signal data sets, among other modality data set discussed herein) acquired from a plurality of clinical studies to be used for the assessment of a given clinical application. For example, for the clinical evaluation system (e.g., 103) used to assess for elevated LVEDP, the training data set repository 612 can include cardiac and photoplethysmographic signals.

The training data set repository 1108 may be used to store labeled data sets for other clinical applications as discussed herein.

Univariate Feature Selection module. The univariate feature selection module 612 is configured to assess the available features (e.g., from modules 122' and/or 608) having greater diagnostic utility than their counterparts, e.g., to reduce feature overfitting to the training data that can lead to poor generalization of the model when it is applied to new unseen data. Development system 104 may employ the univariate feature selection module 612 and the feature importance permutation module 616 to select a subset of optimal features to be used in the model development, e.g., performed by the model development module 610. Features that pass either the first and/or both assessment stages (e.g., via modules 612, 616) may be used in the model development module 610. Univariate feature selection modules 612 may be used for various clinical applications discussed herein, including for (i) heart failure (e.g., left-side or right-side heart failure; heart failure with preserved ejection fraction (HFpEF)), (ii) coronary artery disease (CAD), (iii) various forms of pulmonary hypertension (PH) including without limitation pulmonary arterial hypertension (PAH), (iv) abnormal left ventricular ejection fraction (LVEF), and various other diseases or conditions.

Univariate feature selection module 612 can evaluate many scenarios, each defined by a negative and a positive dataset pair using t-test, mutual information, and AUC-ROC evaluation. The t-test is a statistical test that can determine if there is a difference between two sample means from two populations with unknown variances. Here, the t-tests were conducted against a null hypothesis that there is no difference between the means of the feature in these groups, e.g., normal LVEDP vs. elevated (for LVEDP algorithm development); CAD– vs. CAD+ (for CAD algorithm development). A small p-value (e.g., $\leq 0.05$) indicates strong evidence against the null hypothesis. Mutual information (MI) operations were conducted to assess the dependence of elevated or abnormal LVEDP or significant coronary artery disease on certain features.

An MI score greater than one indicates a higher dependency between the variables being evaluated. MI scores less than one indicate a lower dependency of such variables, and an MI score of zero indicates no such dependency.

A receiver operating characteristic curve, or ROC curve, illustrates the diagnostic ability of a binary classifier system as its discrimination threshold is varied. The ROC curve may be created by plotting the true positive rate (TPR) against the false positive rate (FPR) at various threshold settings. AUC-ROC quantifies the area under a receiver operating characteristic (ROC) curve—the larger this area, the more diagnostically useful the model is. The ROC, and AUC-ROC, value is considered statistically significant when the bottom end of the 95% confidence interval is greater than 0.50.

Table 2 shows an example list of the negative and a positive dataset pair used in the univariate feature selection assessments. Specifically, Table 2 shows positive datasets being defined as having an LVEDP measurement greater than 20 mmHg or 25 mmHg, and negative datasets were defined as having an LVEDP measurement less than 12 mmHg or belonging to a patient group determined to have normal LVEDP readings.

TABLE 2

| Scenario Number | Negative Dataset | Positive Dataset |
| --- | --- | --- |
| 1 | ≤12 mmHg | ≥20 mmHG |
| 2 | ≤12 mmHg | ≥25 mmHG |
| 3 | Negative elevated LVEDP | ≥25 mmHG |
| 4 | Negative elevated LVEDP | ≥20 mmHG |

In the example of the assessment for elevated LVEDP, as a clinical application, results from the univariate feature selection module 616 are provided in: U.S. Provisional Patent Application No. 63/236,072, filed Aug. 23, 2021, entitled "Methods and Systems for Engineering Visual Features From Biophysical Signals for Use in Characterizing Physiological Systems"; U.S. Provisional Patent Application No. 63/235,963, filed Aug. 23, 2021, entitled "Methods and Systems for Engineering Power Spectral Features From Biophysical Signals for Use in Characterizing Physiological Systems"; U.S. Provisional Patent Application No. 63/235,966, filed Aug. 23, 2021, entitled "Method and System for Engineering Rate-Related Features_From Biophysical Signals for Use in Characterizing Physiological Systems"; U.S. Provisional Patent Application No. 63/235,968, filed Aug. 23, 2021, entitled "Methods and Systems for Engineering Wavelet-Based Features From Biophysical Signals for Use in Characterizing Physiological Systems"; U.S. Provisional Patent Application No. 63/130,324, titled "Method and System to Assess Disease Using Cycle Variability Analysis of Cardiac and Photoplethysmographic Signals"; U.S. Provisional Patent Application No. 63/235,971, filed Aug. 23, 2021, entitled "Methods and Systems for Engineering photoplethysmographic Waveform Features for Use in Characterizing Physiological Systems"; U.S. Provisional Patent Application No. 63/236,193, filed Aug. 23, 2021, entitled "Methods and Systems for Engineering Cardiac Waveform Features From Biophysical Signals for Use in Characterizing Physiological Systems"; U.S. Provisional Patent Application No. 63/235,974, filed Aug. 23, 2021, entitled "Methods and Systems for Engineering Conduction Deviation Features From Biophysical Signals for Use in Characterizing Physiological Systems," each of which is hereby incorporated by reference herein in its entirety. In the example of the assessment for significant coronary arterial disease, as another clinical application, results from the univariate feature selection modules 1112 are provided in the U.S. patent application Ser. No. 16/831,264, entitled "Method and System to Assess Disease Using Dynamical Analysis of Biophysical Signals"; and U.S. patent application Ser. No. 16/831,380, entitled "Method and System to Assess Disease Using Dynamical Analysis of Cardiac and Photoplethysmographic Signals," each of which is hereby incorporated by reference herein in its entirety.

For the assessment of significant coronary arterial disease, Univariate feature selection module 612 may perform the assessment on paired data between patients having significant lesions in at least two of three major coronary arteries (positive dataset) and patients having no lesions (negative dataset). Examples of other negative data sets that may be used include healthy control patients, patients with negative diagnostic tests (e.g., as determined using computed tomographic angiography) who do not proceed to cardiac catheterization, and patients who are subjected to angiography but were deemed to have no coronary lesions.

Feature Importance Permutation Analysis Module. The feature importance permutation analysis module 616 is configured to perform additional assessments subsequent to model generation to reduce the number of selected features and their associated models. Feature importance permutation analysis module 616 can generate a permutation importance metric that quantifies the utility of the feature in combination with all other features included in the model generation process. Feature importance permutation analysis module 616 can act as a part of a secondary feature assessment stage that can further limit the number of selected features used in the development of some base models to provide further and more rigorous overfitting control to produce a more stable performance on unseen data.

During model generation (e.g., via Module 610 described below), a large set of models may be generated (e.g., 10,000 models) using a portion of the training data (e.g., 80% of the training data by random sampling) and the rest used for testing. After the training operation, Feature importance permutation analysis module 616 can assess the features within each model using a feature-specific measure relating to permutation importance (or sensitivity). Permutation importance may be applied to Random Forests and various other classifier and machine learning models described herein. Feature importance permutation analysis module 616 can permutate the value of each feature such that each patient's feature value is assigned to a different patient to assess whether the feature is important in rendering the model estimation by determining if a given permutation operation causes a significant detriment to the estimation performance. A feature that causes greater detriment to the model performance when permuted as compared to another feature thus has greater permutation importance.

Intuitively, the permutation importance metric can assess the value that each feature contributes to a model. In some implementations, for a given model, Feature importance permutation analysis module 616 can first compute an initial estimation of the patient's score (e.g., 118) and AUC. Feature importance permutation analysis module 616 can then randomly permutate the values of only a specific feature to recompute the estimation for the score and the revised AUC. The difference between the AUC before and after applying the permutation is the permutation importance of the selected feature. The process can be repeated for all the models and all the features within the models. Feature importance permutation analysis module 616 can assign each feature a permutation importance value using the average of its permutation importance from models that contained that feature as an input.

Model Development Module. The model development module 610 is configured to perform machine learning operations using selected features and labeled data (i.e., data with known disease status) having passed univariate feature selection (e.g., via module 612. Machine learning operations may include but are not limited to linear models, decision trees, random forests, support vector machine, and neural networks such as Random Forest, XGBoost, and Elastic Net models.

Linear models and their variants (e.g., regularized linear models) generate a linear combination of the input features. Decision trees (e.g., gradient boosted decision tree such as XGBoost classifier) generates a series of decisions based on feature thresholds until the output is determined. Random forests generate a collection of decision trees in which each decision tree is trained on various subsets of the training data and the features. Support vector machines generate linear or non-linear classification by mapping the features into a high-dimensional feature space using a kernel operator and then defining a maximally separating hyperplane in that high-dimensional space. Neural networks generate a group of connected units (inspired by a biological neural network) typically organized into an input layer, a set of hidden layers (that can perform linear and non-linear transformations to the features), and an output layer. The ML algorithm, along with its hyper-parameters, may then be determined per the set of available features and per the problem domain.

In one example, the XGBoost Classifier can be performed with hyperparameters comprising a learning rate of 0.5, maximum depth of 3, minimum child weight of 3, 100 total estimators, and a regularization alpha of 0.1. System 103 may use the XGBoost classifier model, e.g., comprising 162 features generated from multiple test labels, including LVEDP≤12 vs. LVEDP≥20, Healthy control group 1 (comprising younger healthy controls) vs. LVEDP≥20, Healthy control group 2 (comprising older healthy controls) vs. LVEDP≥20.

Once the machine learning models (e.g., classifier models 606) have been generated, Module 610 can perform cross-validation operations to reduce overfitting and ensure a certain level of robustness in the estimation (e.g., of score 118) using the machine learning model.

Cross-validation may be performed in an iterative manner in which data is sampled from the available dataset using stratification that samples the data with appropriate weighting in the sampling to ensure an expected representation from both the disease positive and negative groups until a certain percentage of the data has been chosen for training (e.g., 75%-90%). The remaining data can be reserved for validation. A given classifier model is configured and/or optimized using a training data set and then tested on a validation data set. The process may be repeated X times (e.g., 100 times to capture the variability of test performance), resulting in X performance values from which an average performance and variation (such as standard deviation or 95% confidence intervals) can be calculated.

In some embodiments, stratified k-fold cross-validation is performed in which the data is divided while preserving class ratios into k groups or folds. One-fold may be kept for testing, and the model is trained on remaining data (k−1 folds), and the performance metric is evaluated on the testing fold. The process may be repeated k times in which each time for a different fold used for testing and average performance is computed by taking the mean performance of the k folds. The result may be a robust estimate of the performance as it eliminates the errors introduced by random chance. Examples of other cross-validation operations that may be used include Y. Zhang et al., "Facial Emotion Recognition Based on Biorthogonal Wavelet Entropy, Fuzzy Support Vector Machine, and Stratified Cross Validation," in IEEE Access, vol. 4, pp. 8375-8385, 2016; and Mancuso et al., "Sequential testing in high stakes OSCE: a stratified cross-validation approach," MedEdPublish, 8, 62 (2019).

Figures 7A, 7B:
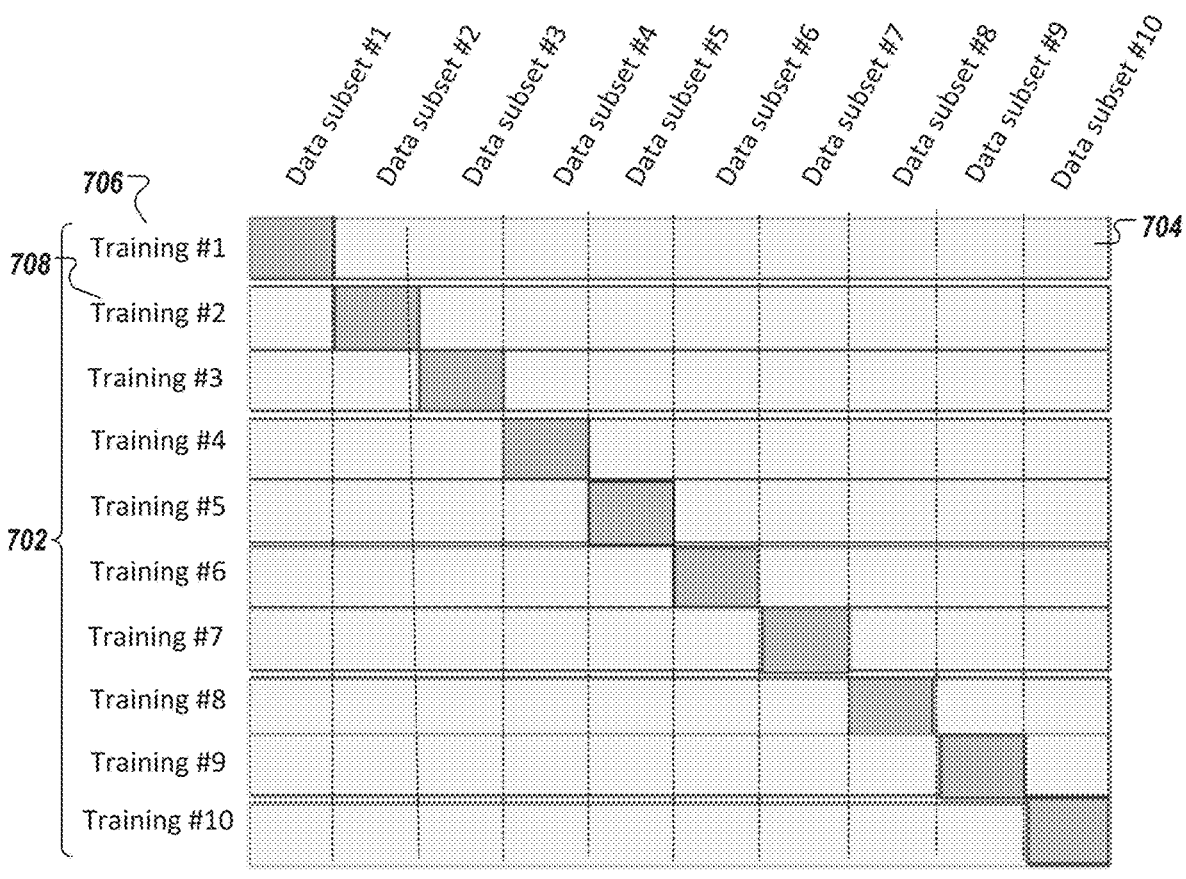
FIGS. 7A-7C shows aspects of the operation of the modules of the development system and environment of FIG. 6.

FIG. 7A shows an example 10-fold cross-validation setup in which the ML algorithm is trained ten times (702) using a different subset of input data (non-highlighted segment in each row) (704). The performance metric may be calculated for each of these ten trained models using the test data (highlighted block in each row). For example, in the example shown in FIG. 7A, the first model 706 (training #1) is generated using training data subset #2 to #10, and the second model 708 (training #2) is generated using training data subset #1 and #3 to #10, and so forth. The average performance of these ten models on each of their respective test data is reported as the model performance.

To further increase the robustness, variability of the expected performance may be reduced by performing multiple iterations of the cross-validation, e.g., shown in FIG. 7A, with different folds from the same data. The results are combined from the multiple rounds to derive tighter bounds of expected performance. Examples of a cross-validation software framework (CV Framework) that may be used include the open-source ML library sci-kit-learn as described in Pedregosa, Fabian, et al. "Scikit-learn: Machine learning in Python." The Journal of Machine Learning Research 12 (2011): 2825-2830. The training of models may be performed on various training sets with different characteristics.

The multiple training operations can generate a plurality of models that can be combined in an ensemble operation. Combining models in the ensemble operation can improve the balance between underfitting and overfitting. In underfitting, a model cannot sufficiently capture the complexity of the relationship between the features and label in the training data, resulting in poor performance in both the training data and unseen test data. In overfitting, a model has leveraged spurious relationships between the features and labels in the training data, causing high performance on the training data that drops when those expected spurious relationships are not present in unseen data. Combining models using ensemble techniques allows these two effects to be balanced by either attempting to reduce overfitting when constituent models have higher performance on the training data or attempting to reduce underfitting when constituent models have lower performance on training data with the overall goal of maximizing performance on unseen data.

In the example for LVEDP assessment, Model development module 610 generated 13 sets of ML models using the ML algorithms described herein. For the ensemble operation, Model development module 610 can perform the operation as disclosed in relation to the description of FIG. 1. Analytical engine or analyzer (e.g., 806, 814—see FIG. 8) can also average the model estimation with a sigmoid function of the patient BMI having the form (sigmoid(x)=1/1+e$^{-x}$).

Hyperparameter Sensitivity Module. Hyperparameter sensitivity analysis module 614 is configured to select a subset of the model, e.g., generated from machine learning (ML) experiments (e.g., among a set of 10-20). An ML Experiment can be defined as a single selection for each feature assessment, dataset, and classifier. Within an ML experiment, ML models can be generated using potentially hundreds of hyperparameters and options. In the example of elevated LVEDP assessment, Hyperparameter sensitivity analysis module 614 conducted 13 ML experiments based on their average performance across about 100 hyperparameter options, including cross-validation, test performance, and performance on the complete dataset and healthy controls.

Hyperparameter sensitivity analysis module 614 can analyze the sensitivity of the model in the sets of ML experiments to reduce the set down to a single model for each experiment. Hyperparameter sensitivity analysis module 614 can calculate a "hyperparameter sensitivity score" to identify hyperparameters with very little effect on the performance (i.e., changing their values does not affect performance) and hyperparameters that are influential. Hyperparameter sensitivity analysis module 614 can first assess the effect on specific regions of hyperparameters, e.g., where certain values of the hyperparameter may result in very similar performances, but other values can cause the performance to jump or fall. Hyperparameter sensitivity analysis module 614 can then assess the models with the hyperparameters having the higher hyperparameter sensitivity score (e.g., 3-5 hyperparameters from an initial 100's).

The hyperparameter sensitivity score can be used to quantify the "stability" of a given model's hyperparameters—e.g., the degree to which the performance of the model can change when compared to the direct neighbors of a model. Hyperparameter sensitivity analysis module 614 can change one hyperparameter at a time in single discrete steps. If the hyperparameter sensitivity score value is close to zero, then the hyperparameters can be considered robust since a small perturbation was observed to not cause a significant change in performance (a desirable property). In the example shown in FIG. 7B, a score (710) for a model (having a value of 0.67) is compared to the scores of its neighbors (712, 714, 716, and 718) (having values of 0.64, 0.68, 0.65, and 0.66). The scores are generated in FIG. 7B for two hyperparameters "A" and "B" that are varied among "1", "2", "3" and among "0.1", "0.5", "0.9," respectively. The difference between the score 710 and the average of the neighbors (712, 714, 716, and 718) in this example is 0.01, which indicates that the hyperparameter and its values (shown as 720 and 722) used to generate the model score (710) are relatively stable and can provide slightly higher performance as compared to its neighboring parameters and their associated values (724).

Figure 7C:
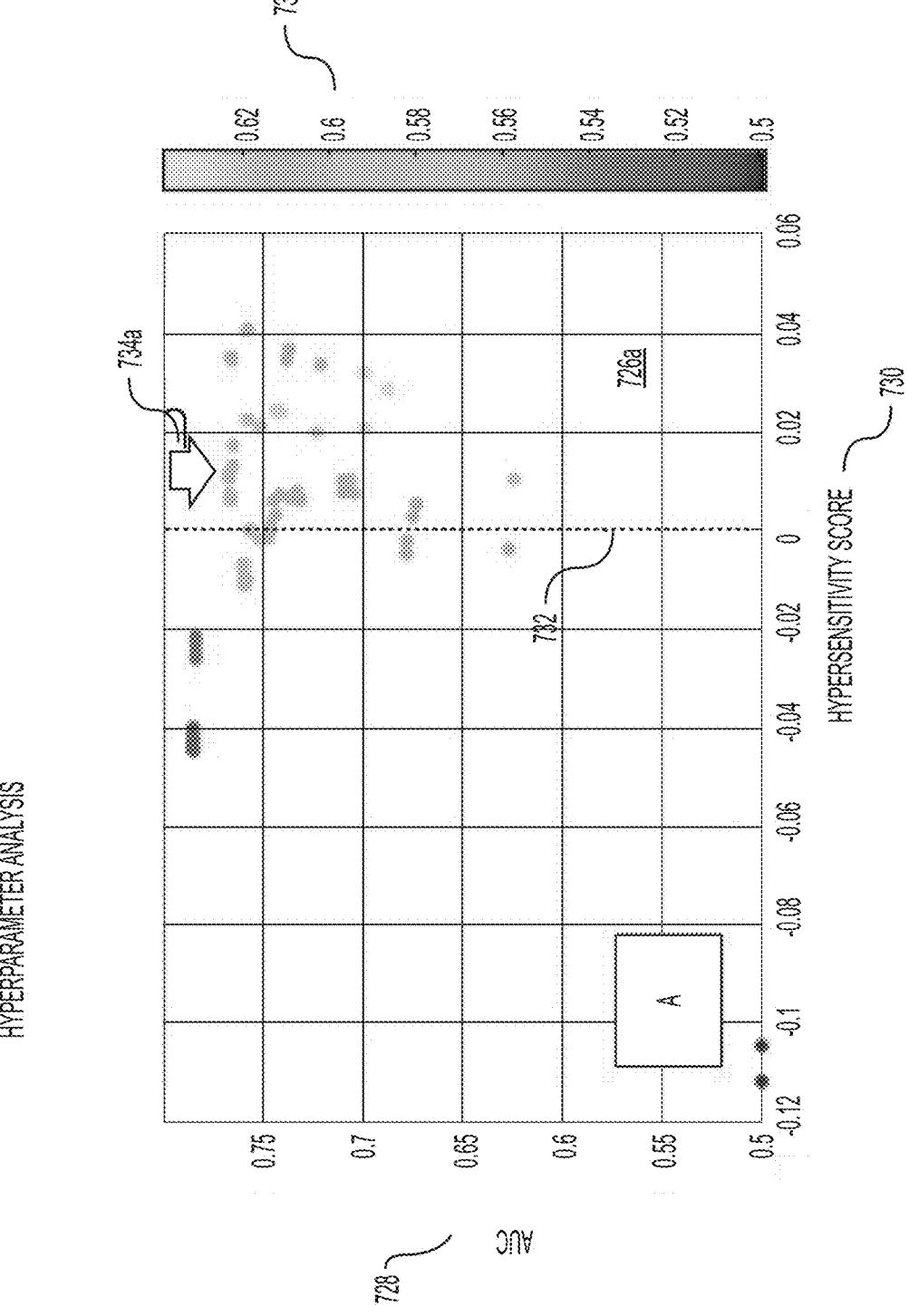
Figure 7C:
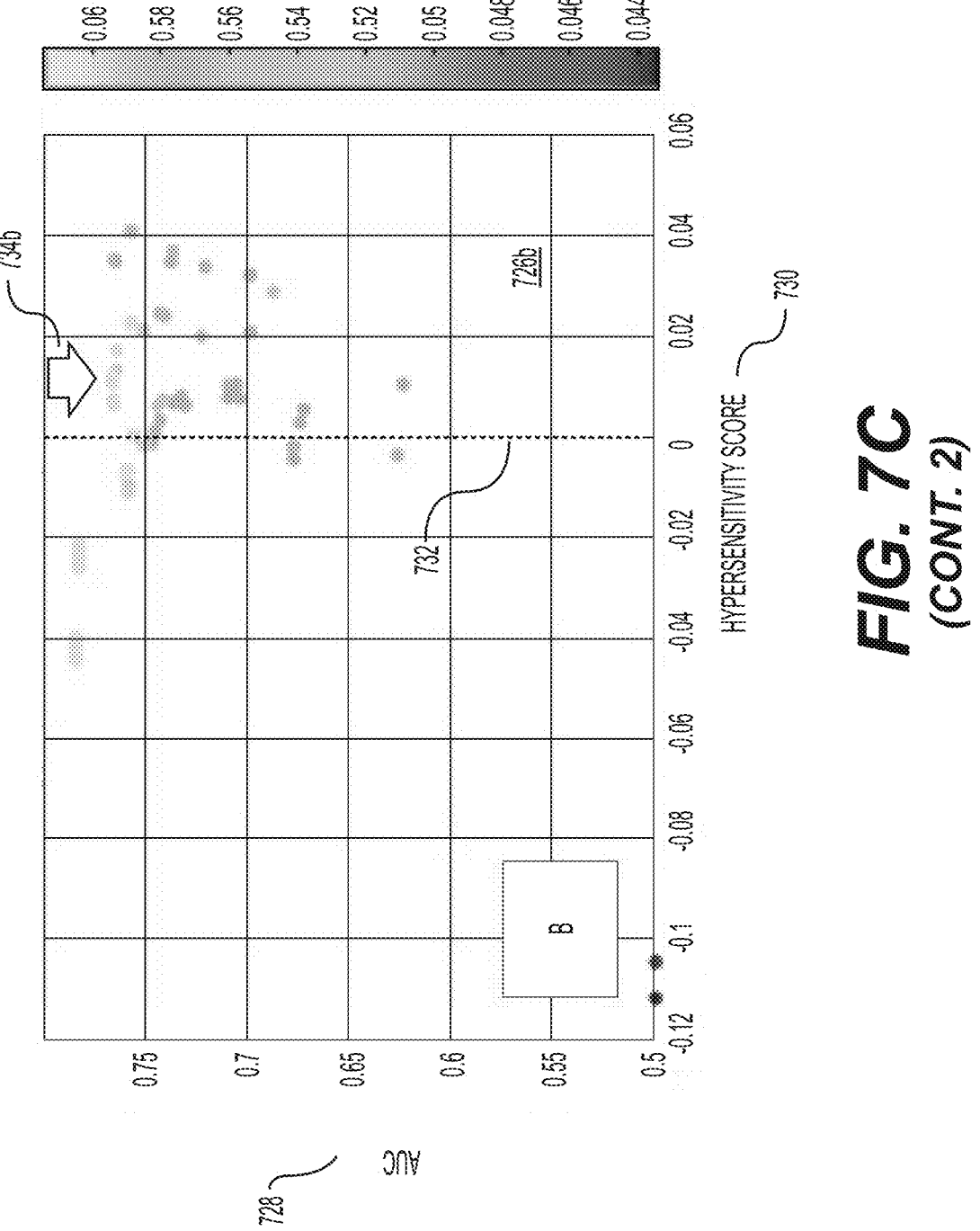
Figure 7C:
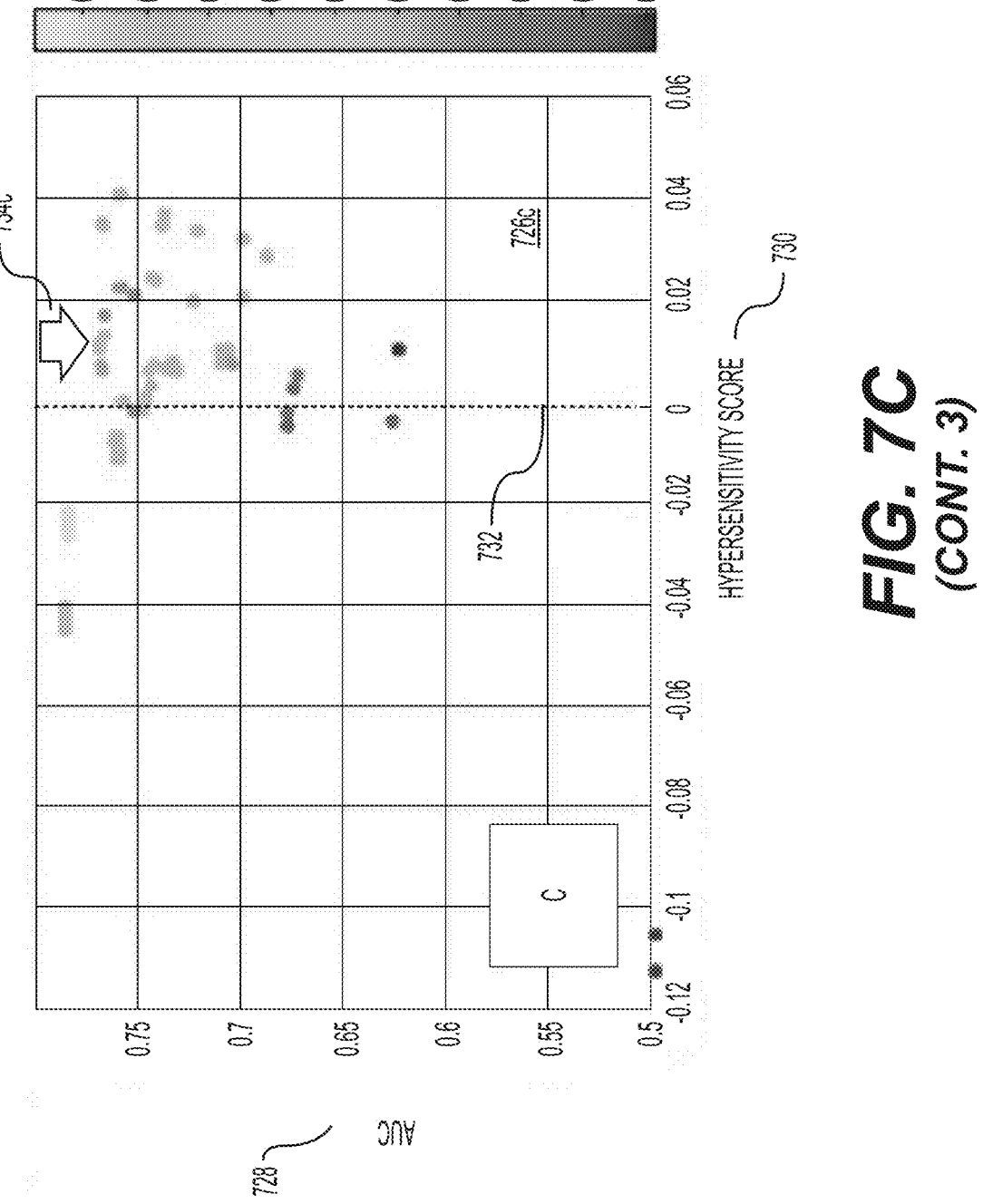
Figure 7C:
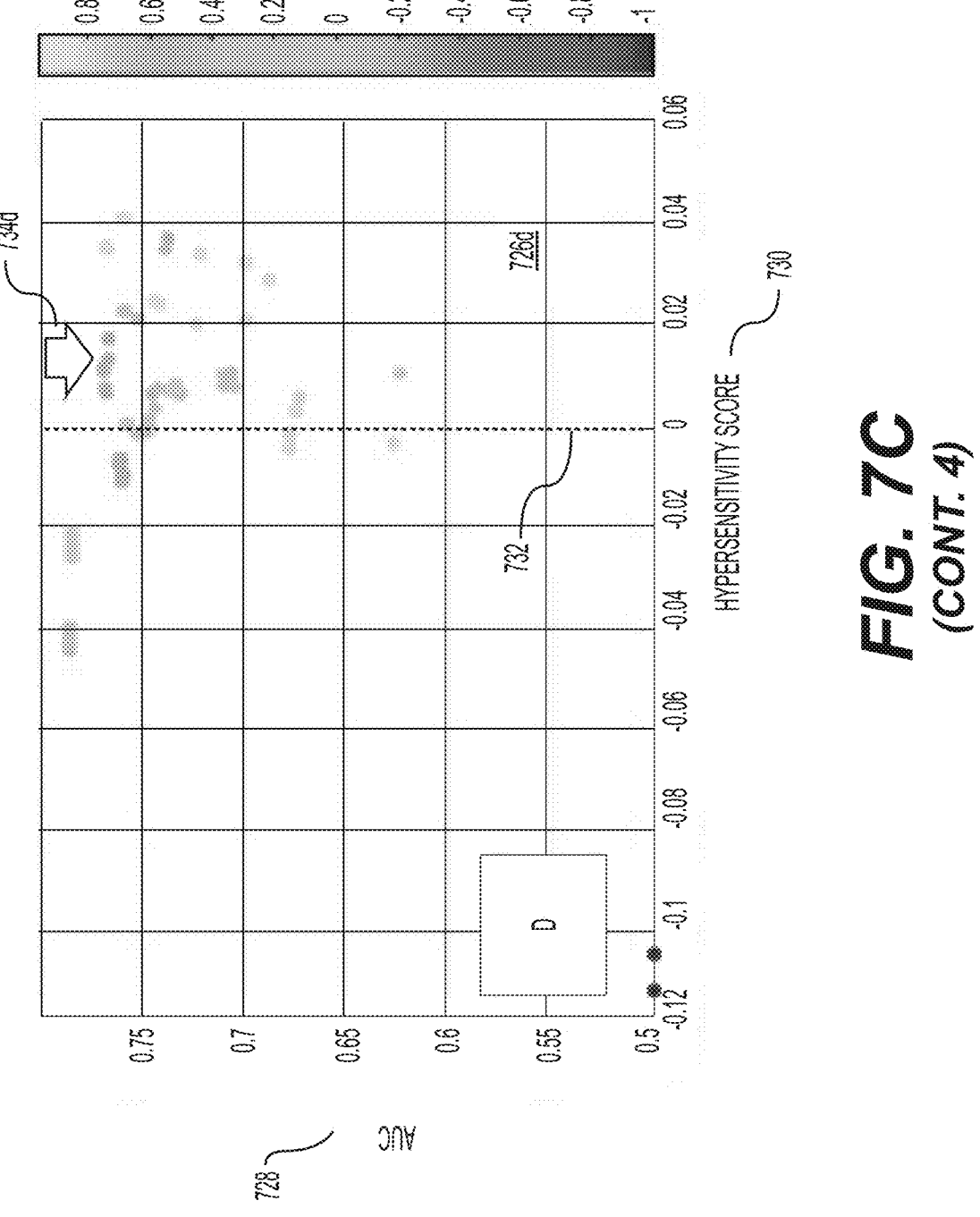

FIG. 7C shows an example use of the hyperparameter sensitivity score for model selection. In FIG. 7C, each of the four subplots (726a, 726b, 726c, 726d). In each of the subplot, the y-axis (728) is the sensitivity score, and the x-axis (730) is the calculated AUC value for a given data set. Looking at 7C, the four subplots (726a, 726b, 726c, 726d) are grouped around a score of zero (732), which is an advantageous property since it indicates the stability of the model hyperparameters. However, it can be observed that some models drift away from zero, some of which have higher performance on the training dataset, and some lower. Despite some of these models having higher performance, they may not be preferred or selected since a slight change in their hyperparameters would cause a change in performance. Therefore, Hyperparameter sensitivity analysis module 614 can select a model close to zero having a cluster indicated by arrows 734a, 734b, 734c, 734d that has maximal performance while still being close to a score of zero. The plotted values of each subplot show different properties of the various models.

In subplot 726a, plotted values indicate the mean test AUC from a cross-validation analysis. If this value is low, then the model does not appear to perform well compared to other models in the experiment. This selected model should have a value that is at least average and, ideally, better than average. The model highlighted by the arrow 734a has a test AUC of around 0.60 (736). Subplot 726b shows plotted values indicating the standard deviation of the test AUC. The selected model should have a low value, which indicates stability. Subplot 726c shows plotted values indicating the average sensitivity and specificity for a given data set. This selected model should have a value that is at least average and, ideally, better than average. Subplot 726d shows plotted values indicating the average specificity for a given data set. It is observed that there is not a significant variation among the models. Indeed, any of the marked models can be selected as they will yield similar results.

Example Clinical and Diagnostic System

Figure 8:
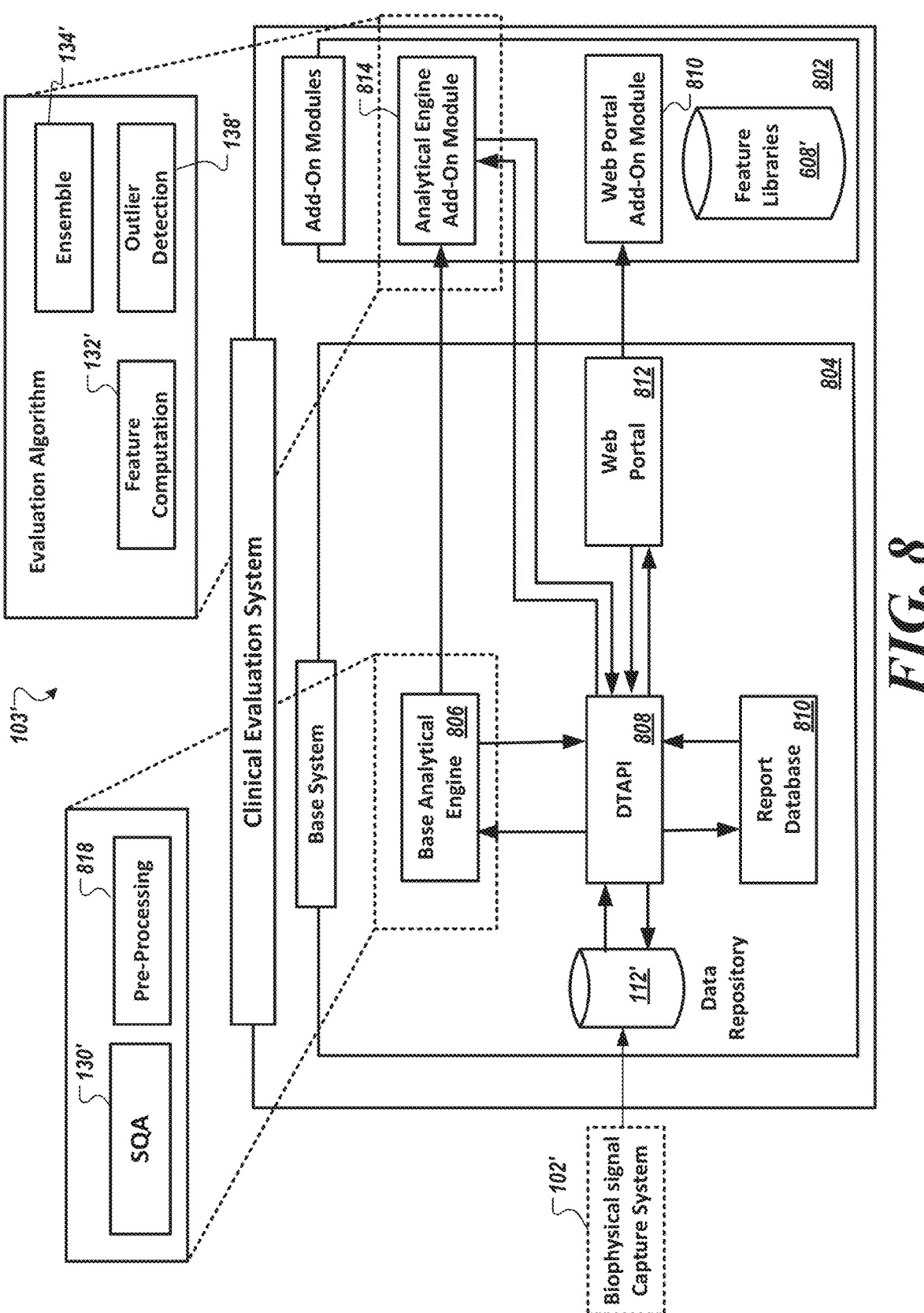
FIG. 8 shows a schematic diagram of an example implementation of the clinical evaluation system of FIG. 1.

FIG. 8 shows an example clinical evaluation system 103 (shown as 103') that implements the modules of FIG. 1 to non-invasively estimate one or more metrics associated with the physiological state of a patient according to an embodiment. Indeed, the feature modules (e.g., of FIG. 1) can be generally viewed as a part of a system (e.g., the clinical evaluation system 103') in which any number and/or types of features may be utilized for a disease state, medical condition, an indication of either, or combination thereof that is of interest, e.g., with different embodiments having different configurations of feature modules. FIG. 8 further illustrates the clinical evaluation system 800 as a modular system in which disease-specific add-on modules 802 (e.g., to assess for elevated LVEDP or mPAP, CAD, PH/PAH, abnormal LVEF, HFpEF, and others described herein) are capable of being integrated alone or in multiple instances with a singular platform (i.e., a base system 804) to realize system's (e.g., 103') full operation. The modularity allows the clinical evaluation system 103' to be designed to leverage the same synchronously acquired biophysical signals and data set and base platform to assess for the presence of several different diseases as such disease-specific algorithms are developed, thereby reducing testing and certification time and cost.

In various embodiments, as shown in FIGS. 1 and 8, different versions of the clinical evaluation system (e.g., 103, 103') may be implemented by having included different feature computation modules (e.g., 132, 132') that can be configured for a given disease state(s), medical condition(s), or indicating condition(s) of interest. In another embodiment, the clinical evaluation system (e.g., 103, 103') may include more than one such system and may be selectively utilized to generate different scores specific to a classifier (shown as 134, 134') of that engine (e.g., 103, 103'). In this way, the modules of FIGS. 1 and 8 in a more general sense may be viewed as one configuration of a modular system in which different and/or multiple engines (e.g., 103, 103'), with different and/or multiple corresponding classifiers (e.g., 134, 134'), may be used depending on the configuration of module desired.

In the example shown in FIG. 8, Clinical evaluation system 103' can analyze one or more biophysical-signal data sets (e.g., 110 in FIG. 1) from repository 112 (shown as 112') using machine-learned disease-specific algorithms to assess the likelihood of a disease, condition, or indication of either, such as elevated LVEDP as one example. Clinical evaluation system 103' includes hardware and software components that are designed to work together in combination to facilitate the analysis and presentation of an estimation score using the algorithm to allow a physician to use that score, e.g., to assess for the presence or non-presence of a disease state, medical condition, or an indication of either.

The base system 804 can provide a foundation of functions and instructions upon which each add-on module 802 (which includes the disease-specific algorithm) then interfaces to assess for the pathology or indicating condition. The base system 804, as shown in the example of FIG. 8, includes a base analytical engine or analyzer 806, a web-service data transfer API 808 (shown as "DTAPI" 808), a report database 810, a web portal service module 812 (e.g., implementing the physician portal visualization 136), and the data repository 112'.

Data repository 112', which can be cloud-based, stores data from the signal capture system 102 (shown as 102'). Biophysical signal capture system 102' can be a reusable device designed as a single unit, e.g., with a seven-channel lead set for cardiac signal acquisition and photoplethysmogram (PPG) sensor securely attached (i.e., not removable). Signal capture system 102', together with its hardware, firmware, and software, provides a user interface to collect patient-specific metadata entered therein (e.g., name, gender, date of birth, medical record number, height, and weight, etc.) to synchronously acquire the patient's electrical and hemodynamic signals. The signal capture system 102' may securely transmit the metadata and signal data as a single data package directly to the cloud-based data repository. The data repository 112', in some embodiments, is a secure cloud-based database configured to accept and store the patient-specific data package and allow for its retrieval by the analytical engines or analyzer 806 or 814.

Base analytical engine or analyzer 806 can be a secure cloud-based processing tool that may perform quality assessments of the acquired signals (e.g., performed via "SQA" module 130 (shown as 130')), the results of which can be communicated to the physician or patient at the point of care. The base analytical engine or analyzer 806 may also perform pre-processing (shown via pre-processing module 818) of the acquired biophysical signals (e.g., 110—see FIG. 1). Web portal 812 is a secure web-based portal configured to provide healthcare providers access to the patient's reports. An example output of the web portal 812 is shown by visualization 136 (also referenced as 402) (see FIGS. 1 and 4). The report databases 810 is a secure database and may securely interface and communicate with other systems, such as a hospital or physician-hosted, remotely hosted, or remote electronic health records systems (e.g., Epic, Cerner, Allscrips, CureMD, Kareo, etc.) so that output score(s) (e.g., 118) and related information may be integrated into and saved with the patient's general health record. In some embodiments, web portal 812 is accessed by a call center to provide the output clinical information over a telephone. Report database 810 may be accessed by other systems that can generate a report to be delivered via the mail, courier service, personal delivery, etc.

Add-on module 802 includes a second part 814 (also referred to herein as the analytical engine (AE) or analyzer 814 and shown as "AE add-on module" 814) that operates with the base analytical engine (AE) or analyzer 806. Analytical engine (AE) or analyzer 814 can include the main function loop of a given disease-specific algorithm, e.g., the feature computation module 132 (shown as 132'), the classifier model 134 (shown as "Ensemble" 134'), and the outlier assessment and rejection module 138 (shown as "Outlier Detection" 138'). In certain modular configurations, Analytical engines or analyzers (e.g., 806 and 814) may be implemented in a single analytical engine module.

The main function loop can include instructions to (i) validate the executing environment to ensure all required environment variables values are present and (ii) execute an analysis pipeline that analyzes a new signal capture data file comprising the acquired biophysical signals to calculate the patient's score using the disease-specific algorithm. To execute the analysis pipeline, AE add-on module 814 can include and execute instructions for the feature modules 132' and classifier module 134' to determine an output score (e.g., 118—see FIG. 1 or 4) of the metrics associated with the physiological state of a patient. The analysis pipeline in the AE add-on module 814 can compute the features or parameters (via module(s) 132') and can identify whether the computed features are outliers (e.g., via modules 138') by providing an outlier detection return comprising a signal-level response of outlier vs. non-outlier based on the feature. The outliers may be assessed with respect to the training data set used to establish the classifier. AE add-on module 814 can generate the patient's output score (e.g., 118) (e.g., via classier module 134') using the computed values of the features and classifier models. In the example of an evaluation algorithm for the estimation of elevated LVEDP, the output score (e.g., 118) is an LVEDP score.

Clinical evaluation system 800 can manage data within and across components using the web-service DTAPIs 808 (also referred to as HCPP web services in some embodiments). DTAPIs 808 may be used to retrieve acquired biophysical data sets from and to store signal quality analysis results to the data repository 112a. DTAPIs 808 may also be invoked to retrieve and provide the stored biophysical data files to the analytical engines or analyzers (e.g., 806, 814). The results of the analytical engine's analysis of the patient signals may be transferred using DTAPI 808 to the report database 810. DTAPIs 808 may also be used, upon a request by a healthcare professional, to retrieve a given patient data set to the web portal module 812, which may present a report to the healthcare practitioner for review and interpretation in a secure web-accessible interface.

Clinical evaluation system 800 can include one or more feature libraries 608, or portions thereof (shown as 608') that store the feature modules 132'. The feature libraries 608' may be a part of the add-on modules 802 (as shown in FIG. 8) or the base system 804 (not shown) and are accessed, in some embodiments, by the AE add-on module 814.

Further details of the modularity of modules and various configurations are provided in a provisional patent application currently filed herewith and 63/234,772, which is hereby incorporated by reference herein in its entirety.

While the methods and systems have been described in connection with certain embodiments and specific examples, it is not intended that the scope be limited to the particular embodiments set forth, as the embodiments herein are intended in all respects to be illustrative rather than restrictive. The clinical evaluation system and method discussed herein may be employed to make, or to assist a physician or other healthcare provider in making, noninvasive diagnoses or determinations of the presence or non-presence and/or severity of other diseases and/or conditions, such as, e.g., coronary artery disease, pulmonary hypertension and other pathologies as described herein using similar or other development approaches. In addition, the example clinical evaluation system and method can be used in the diagnosis and treatment of other cardiac-related pathologies and conditions as well as neurological-related pathologies and conditions, such assessment can be applied to the diagnosis and treatment (including surgical, minimally invasive, and/or pharmacologic treatment) of any pathologies or conditions in which a biophysical signal is involved in any relevant system of a living body. One example in the cardiac context is the diagnosis of CAD and other diseases and conditions disclosed herein and its treatment by any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/ nerve injury, chronic traumatic encephalopathy, cluster headaches, migraine headaches, neuropathy (in its various forms, including peripheral neuropathy), phantom limb/ pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

In addition, the clinical evaluation system described herein may be configured to analyze biophysical signals such as an electrocardiogram (ECG), electroencephalogram (EEG), gamma synchrony, respiratory function signals, pulse oximetry signals, perfusion data signals; quasi-periodic biological signals, fetal ECG signals, blood pressure signals; cardiac magnetic field signals, heart rate signals, among others.

Further examples of processing that may be used with the exemplified method and system disclosed herein are described in: U.S. Pat. Nos. 9,289,150; 9,655,536; 9,968,275; 8,923,958; 9,408,543; 9,955,883; 9,737,229; 10,039,468; 9,597,021; 9,968,265; 9,910,964; 10,672,518; 10,566,091; 10,566,092; 10,542,897; 10,362,950; 10,292,596; 10,806,349; U.S. Patent Publication nos. 2020/0335217; 2020/0229724; 2019/0214137; 2018/0249960; 2019/0200893; 2019/0384757; 2020/0211713; 2019/0365265; 2020/0205739; 2020/0205745; 2019/0026430; 2019/0026431; PCT Publication nos. WO2017/033164; WO2017/221221; WO2019/130272; WO2018/158749; WO2019/077414; WO2019/130273; WO2019/244043; WO2020/136569; WO2019/234587; WO2020/136570; WO2020/136571; U.S. patent application Ser. Nos. 16/831,264; 16/831,380; 17/132,869; PCT Application nos. PCT/IB2020/052889; PCT/IB2020/052890, each of which has been incorporated by reference herein in its entirety.

The following patents, applications, and publications as listed below and throughout this document are hereby incorporated by reference in their entirety herein.

LIST OF REFERENCES

[1] Y. Zhang et al., "Facial Emotion Recognition Based on Biorthogonal Wavelet Entropy, Fuzzy Support Vector Machine, and Stratified Cross Validation," in IEEE Access, vol. 4, pp. 8375-8385, 2016, doi: 10.1109/ACCESS.2016.2628407.
[2] Mancuso G, Strachan S, Capey S, 2019, 'Sequential testing in high stakes OSCE: a stratified cross-validation approach', MedEdPublish, 8, [2], 62, https://doi.org/10.15694/mep.2019.000132.1
[3] Pedregosa, Fabian, et al. "Scikit-learn: Machine learning in Python." The Journal of Machine Learning Research 12 (2011): 2825-2830.
[4] Breiman, "Random Forests," Machine Learning, 45(1), 5-32, 2001.
[5] Chen, Tianqi; Guestrin, Carlos (2016). "XGBoost: A Scalable Tree Boosting System," Proceedings of the 22nd ACM SIGKDD International Conference on Knowledge Discovery and Data Mining, San Francisco, CA, USA, Aug. 13-17, 2016. ACM. pp. 785-794.
[6] H. Zou and T. Hastie, "Regularization and variable selection via the elastic net," Journal of the Roy. Statist. Soc., ser. B, vol. 67, no. 2, pp. 301-320, 2005.
[7] L. Breiman, "Bagging predictors," Machine Learning, 24(2), 123-140, 1996.
[8] Liu, F. T., Ting, K. M. and Zhou, Z. H., 2008, December. Isolation forest. In 2008 eighth IEEE international conference on data mining (pp. 413-422). IEEE.

What is claimed is:

1. A method to non-invasively estimate presence of elevated left-ventricular end diastolic pressure (LVEDP) in a mammalian subject, the method comprising:

obtaining, by one or more processors, a first biophysical signal data set associated with a first photoplethysmographic signal and a second photoplethysmographic signal, wherein the first biophysical data set has been acquired over multiple cardiac cycles of the subject;

obtaining, by the one or more processors, a second biophysical signal data set associated with a cardiac signal, wherein the second biophysical data set has been simultaneously acquired with the first biophysical signal data set over the multiple cardiac cycles;

determining, by the one or more processors utilizing at least a portion of the first and second biophysical signal data sets, a plurality of values associated with a plurality of features; and determining, by the one or more processors, an estimated value for presence of elevated left-ventricular end diastolic pressure using the plurality of values associated with the plurality of features quantifying synchronicity between the cardiac signal and the first and the second photoplethysmographic signals and the plurality of features associated with respective cardiac signal and the first and the second photoplethysmographic signals, wherein the estimated value for presence of elevated left-ventricular end diastolic pressure values is determined by determining a plurality of values for the plurality of features in two or more models, model selected from the group consisting of a linear model, a decision tree model, a random forest model, a support vector machine model, a neural network model, and wherein the two or more models are combined in an ensemble model that averages outputs of the two or more models to generate the estimated value for the presence of elevated left-ventricular end diastolic pressure, wherein the estimated value for the presence of elevated left-ventricular end diastolic pressure is outputted for use in a diagnosis of expected left heart failure (LHF) or to direct treatment of the expected left heart failure.

2. The method of claim 1, wherein the one or more processors are located in a cloud platform or a local computing device.

3. The method of claim 1 further comprising:

preprocessing, by the one or more processors, the second biophysical signal data set, wherein the preprocessing includes transient time removal operation, DC offset removal operation, and baseline wander removal operation.

4. The method of claim 1 further comprising:

determining, by the one or more processors, via a signal quality assessment analysis of the first biophysical signal data set, a plurality of photoplethysmographic noise scores of the first biophysical signal data set, including i) a first photoplethysmographic noise score associated with rapid changes in the first or second photoplethysmographic signals and ii) a second photoplethysmographic noise score associated with measurement saturation.

5. The method of claim 1 further comprising:

determining, by the one or more processors, via a signal quality assessment analysis of the second biophysical signal data set, a plurality of biopotential noise scores of the second biophysical signal data set, including a first biopotential noise score associated with biopotential powerline interference and a second biopotential noise score associated with bipotential high frequency noise.

6. The method of claim 1, wherein the ensemble model includes at least the two or more models and a model associated with a body mass index (BMI) value of the mammalian subject.

7. The method of claim 1, further comprising:

removing a feature from a plurality of candidate features having a high occurrence of extraction errors.

8. The method of claim 1, wherein the plurality of features are configured in a machine-learned model, wherein the machine-learned model is trained using hyperparameters selected from a group of hyperparameters that have been evaluated in a hyperparameter sensitivity analysis.

9. The method of claim 1, wherein the plurality of features include a feature set selected from the group consisting of:

one or more depolarization or repolarization wave propagation associated features;

one or more depolarization wave propagation deviation associated features;

one or more cycle variability associated features;

one or more dynamical system associated features;

one or more cardiac waveform topologic and variations associated features;

one or more PPG waveform topologic and variations associated features;

one or more cardiac or PPG signal power spectral density associated features;

one or more cardiac or PPG signal visual associated features; and one or more predictability features.

10. The method of claim 9, wherein the one or more depolarization or repolarization wave propagation associated features are configured to quantify a propagative characteristic of a ventricular depolarization (VD) wave or a ventricular repolarization (VR) wave defined in the cardiac signal in three-dimensional space, wherein the one or more depolarization wave propagation deviation associated features are configured to quantify deviations, via evaluation of high-frequency and low-amplitude patterns, of a VD wave trajectory from a trajectory of a three-dimensional modeled VD wave, wherein the one or more cycle variability associated features are configured to quantify beat-to-beat variations of the cardiac signal in comparison of each respective beat to a determined template beat, wherein the one or more dynamical system features are configured to quantify dynamical characteristics of the second biophysical data set, wherein the one or more cardiac waveform topologic and variations associated features are configured to quantify both cardiac measurements and variations of the second biophysical signal data set, wherein the one or more PPG waveform topologic and variations associated features are configured to quantify both PPG measurements and variations of the first biophysical signal data set, wherein the one or more cardiac or PPG signal power spectral density associated features are configured to quantify a power spectrum and frequency content of the first photoplethysmographic signal and a second photoplethysmographic signal, wherein the one or more cardiac or PPG signal power spectral density associated features are configured to quantify a power spectrum and frequency content of the second biophysical signal data set, wherein the one or more cardiac or PPG visual associated features are configured to quantify geometric parameters of a three-dimensional phase space generated from the first or second biophysical data set, and wherein the one or more predictability features are configured to quantify a predictability measure of the cardiac signal.

11. The method of claim 1 further comprising:

determining, by the one or more processors, via an outlier detection analysis of the first biophysical signal data set and the second biophysical signal data set, presence of outliers, wherein the outlier detection analysis comprises a machine learned module configured to detect arrhythmia and/or incorrect lead configurations in the mammalian subject.

12. The method of claim 11, wherein the machine learned module is further configured to detect an anomalous waveform that is missing or has extra waveform elements in the first photoplethysmographic signal, the second photoplethysmographic signal, and/or the cardiac signal.

13. The method of claim 1, wherein the plurality of features are selected from a pool of candidate features by a selection module, wherein the selection module comprises a univariate feature assessment analysis that evaluates data sets defined with respect to a positive pathology label associated with an elevated LVEDP and a negative pathology label associated with a normal LVEDP.

14. The method of claim 13, wherein the data sets are defined by a positive and negative pathology label selected from the group consisting of:

a LVEDP value greater than or equal to 20 mmHg and a LVEDP value less than or equal to 12 mmHg; and a LVEPD value greater than or equal to 25 mmHg and a LVEDP value less than or equal to 12 mmHg.

15. The method of claim 13, wherein the selection module comprises a cross-validation analysis for a set of trained models, wherein the evaluated data sets are randomly sampled as a training data set and non-selected data sets as a remainder are used as a validation data set in a feature permutation importance analysis, wherein the feature permutation importance analysis quantifies a utility of a feature of the plurality of features in combination with all other assessed features of the plurality of features.

* * * * *